US012589136B2

(12) United States Patent
Thompson et al.

(10) Patent No.: US 12,589,136 B2
(45) Date of Patent: Mar. 31, 2026

(54) VIRAL VECTORS COMPRISING RDH12 CODING REGIONS AND METHODS OF TREATING RETINAL DYSTROPHIES

(71) Applicant: THE REGENTS OF THE UNIVERSITY OF MICHIGAN, Ann Arbor, MI (US)

(72) Inventors: Debra A. Thompson, Ann Arbor, MI (US); Robin R. Ali, London (GB); Alexander J. Smith, London (GB)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 367 days.

(21) Appl. No.: 17/818,623

(22) Filed: Aug. 9, 2022

(65) Prior Publication Data

US 2023/0190884 A1      Jun. 22, 2023

Related U.S. Application Data

(63) Continuation of application No. 16/192,382, filed on Nov. 15, 2018, now abandoned.

(60) Provisional application No. 62/586,624, filed on Nov. 15, 2017.

(51) Int. Cl.
| | |
|---|---|
| *A61K 38/44* | (2006.01) |
| *A61P 27/02* | (2006.01) |
| *C12N 7/00* | (2006.01) |

(52) U.S. Cl.
CPC ............ *A61K 38/443* (2013.01); *A61P 27/02* (2018.01); *C12N 7/00* (2013.01); *C12Y 101/01105* (2013.01); *C12N 2710/10043* (2013.01)

(58) Field of Classification Search
CPC ............ A61P 27/02; C12Y 101/01105; A01K 2267/0306; A61K 48/0058; C12N 15/86
See application file for complete search history.

(56) References Cited

U.S. PATENT DOCUMENTS

| | | | |
|---|---|---|---|
| 10,392,622 | B2 | 8/2019 | Lewis et al. |
| 11,197,936 | B2 | 12/2021 | Bennett et al. |
| 2014/0364488 | A1 | 12/2014 | Pawlyk et al. |
| 2015/0259395 | A1 | 9/2015 | Chalberg et al. |
| 2016/0015288 | A1 | 1/2016 | Neitz et al. |
| 2019/0151473 | A1 | 5/2019 | Bennett et al. |
| 2022/0118110 | A1 | 4/2022 | Bennett et al. |
| 2022/0118111 | A1 | 4/2022 | Bennett et al. |
| 2023/0009257 | A1 | 1/2023 | Bennett et al. |

FOREIGN PATENT DOCUMENTS

| | | |
|---|---|---|
| CA | 3029646 | 1/2018 |
| JP | 2013-526854 | 6/2013 |
| JP | 2017-518271 | 7/2017 |
| SG | 11201607991 W | 10/2016 |
| WO | WO2011034947 A2 | 3/2011 |
| WO | WO2011133933 A2 | 10/2011 |
| WO | WO2012167109 A2 | 12/2012 |
| WO | WO2014011210 A1 | 1/2014 |
| WO | WO2015075154 A2 | 5/2015 |
| WO | WO2015168666 A2 | 11/2015 |
| WO | WO2016001693 A1 | 1/2016 |
| WO | WO2016014353 A1 | 1/2016 |
| WO | WO2016019364 A1 | 2/2016 |
| WO | WO2016145345 A1 | 9/2016 |
| WO | WO2016176690 A2 | 11/2016 |
| WO | WO2018009814 A1 | 1/2018 |
| WO | WO2023129095 A1 | 7/2023 |

OTHER PUBLICATIONS

Dumitrescu et al., 2024 (EyeWiki, Leber Congenital Amaurosis, p. 1-4).*
Drag et al., 2023 (IOVS, vol. 64, No. 7, article 39, p. 1-17).*
Surace et al., 2014 (Geneseq Accession No. BBM84818, computer printout, pp. 1-2).*
Kay et al., 2013 (PLOS ONE, vol. 8, Issue 4, e62097, p. 1-12).*
Berson et al., 2012 (Geneseq Accession No. BAI65575, computer printout, p. 1).*
Acland, Gregory M., et al. "Gene therapy restores vision in a canine model of childhood blindness." Nature genetics 28.1 (2001): 92-95.
Adamian, Michael, et al. "Rod and cone opsin mislocalization in an autopsy eye from a carrier of X-linked retinitis pigmentosa with a Gly436Asp mutation in the RPGR gene." American journal of ophthalmology 142.3 (2006): 515-518.
Alexander, John J., et al. "Restoration of cone vision in a mouse model of achromatopsia." Nature medicine 13.6 (2007): 685-687.
Ali, Robin R., et al. "Restoration of photoreceptor ultrastructure and function in retinal degeneration slow mice by gene therapy." Nature genetics 25.3 (2000): 306-310.
Allocca, Mariacarmela, et al. "Novel adeno-associated virus serotypes efficiently transduce murine photoreceptors." Journal of virology 81.20 (2007): 11372-11380.
Bainbridge, James WB, et al. "Effect of gene therapy on visual function in Leber's congenital amaurosis." New England Journal of Medicine 358.21 (2008): 2231-2239.
Beltran, William A., et al. "Gene therapy rescues photoreceptor blindness in dogs and paves the way for treating human X-linked retinitis pigmentosa." Proceedings of the National Academy of Sciences 109.6 (2012): 2132-2137.

(Continued)

*Primary Examiner* — Valarie E Bertoglio
(74) *Attorney, Agent, or Firm* — Baker, Donelson, Bearman, Caldwell & Berkowitz, PC

(57) ABSTRACT

Provided are compositions useful for treating an ophthalmological condition due to one or more loss-of-function mutations in the gene encoding the Retinol Dehydrogenase 12 (RDH12) protein. Provided herein are nucleic acids encoding a human RDH12 and vectors comprising an expressible coding region for human RDH12. Also provided are uses of such nucleic acids and vectors for treating ophthalmological disease, including, but not limited to Leber Congenital Amaurosis.

12 Claims, 9 Drawing Sheets

Specification includes a Sequence Listing.

(56) References Cited

OTHER PUBLICATIONS

Belyaeva, Olga V., et al. "Biochemical properties of purified human retinol dehydrogenase 12 (RDH12): catalytic efficiency toward retinoids and C9 aldehydes and effects of cellular retinol-binding protein type I (CRBPI) and cellular retinaldehyde-binding protein (CRALBP) on the oxidation and reduction of retinoids." Biochemistry 44.18 (2005): 7035-7047.

Bennett et al., 2019, US 20190151473 A 1, effective filing date, Jul. 8, 2016.

Ben-Shabat, Shimon, et al. "Fluorescent pigments of the retinal pigment epithelium and age-related macular degeneration." Bioorganic & medicinal chemistry letters 11.12 (2001): 1533-1540.

Berson et al., 2013, Geneseq Accession No. BAI65575, computer printout, pp. 1-2.

Bligh, E. Graham, and W. Justin Dyer. "A rapid method of total lipid extraction and purification." Canadian journal of biochemistry and physiology 37.8 (1959): 911-917.

Borel, Jean F., et al. "Biological effects of cyclosporin A: a new antilymphocytic agent." Agents and actions 43 (1994): 179-186.

Brunner, Sandra, et al. "Cone versus rod disease in a mutant Rpgr mouse caused by different genetic backgrounds." Investigative Ophthalmology & Visual Science 51.2 (2010): 1106-1115.

Bryan et al., 2013, http://www.elsevierblogs.com/currentcomments/?p=962, Implications of protein fold switching, p. 1-4.

Chen, Chunhe, Debra A. Thompson, and Yiannis Koutalos. "Reduction of all-trans-retinal in vertebrate rod photoreceptors requires the combined action of RDH8 and RDH12." Journal of Biological Chemistry 287.29 (2012): 24662-24670.

Chen, Yu, et al. "Mechanism of all-trans-retinal toxicity with implications for stargardt disease and age-related macular degeneration." Journal of Biological Chemistry 287.7 (2012): 5059-5069.

Chrispell, Jared D., et al. "Rdh12 activity and effects on retinoid processing in the murine retina." Journal of Biological Chemistry 284.32 (2009): 21468-21477.

Cideciyan, Artur V., et al. "Human gene therapy for RPE65 isomerase deficiency activates the retinoid cycle of vision but with slow rod kinetics." Proceedings of the National Academy of Sciences 105.39 (2008): 15112-15117.

Cruz et al., 2017, Methods in Molecular Biology, vol. 1654, Chapter 5, pp. 55-75.

Den Hollander, Anneke I., et al. "Leber congenital amaurosis: genes, proteins and disease mechanisms." Progress in retinal and eye research 27.4 (2008): 391-419.

European Search Report from Application No. 18878835.0 dated May 18, 2021.

Feathers, Kecia L., et al. "Development of a gene therapy vector for RDH12-associated retinal dystrophy." Human Gene Therapy 30.11 (2019): 1325-1335.

Flotte, Terence R., et al. "Expression of the cystic fibrosis transmembrane conductance regulator from a novel adeno-associated virus promoter." Journal of Biological Chemistry 268.5 (1993): 3781-3790.

Flotte, Terence R., et al. "Gene expression from adeno-associated virus vectors in airway epithelial cells." Am J Respir Cell Mol Biol 7.3 (1992): 349-356.

Georgiadis, A., et al. "Development of an optimized AAV2/5 gene therapy vector for Leber congenital amaurosis owing to defects in RPE65." Gene therapy 23.12 (2016): 857-862.

Haeseleer, Françoise, et al. "Dual-substrate specificity short chain retinol dehydrogenases from the vertebrate retina." Journal of Biological Chemistry 277.47 (2002): 45537-45546.

Hermonat, Paul L., and Nicholas Muzyczka. "Use of adeno-associated virus as a mammalian DNA cloning vector: transduction of neomycin resistance into mammalian tissue culture cells." Proceedings of the National Academy of Sciences 81.20 (1984): 6466-6470.

Hufnagel, Robert B., et al. "Gene therapy for Leber congenital amaurosis: advances and future directions." Graefe's archive for clinical and experimental ophthalmology 250 (2012): 1117-1128.

International Search Report and Written Opinion from International Application No. PCT/US18/61319 dated Feb. 12, 2019.

Janecke, Andreas R., et al. "Mutations in RDH12 encoding a photoreceptor cell retinol dehydrogenase cause childhood-onset severe retinal dystrophy." Nature genetics 36.8 (2004): 850-854.

Kasus-Jacobi et al., "Mechanisms of RDH12-Induced Leber Congenital Amaurosis and Therapeutic Aooroaches," Advances In Ophthalmology, 25 pages (2012).

Keller, Brigitte, and Jerzy Adamski. "RDH12, a retinol dehydrogenase causing Leber's congenital amaurosis, is also involved in steroid metabolism." The Journal of Steroid Biochemistry and Molecular Biology 104.3-5 (2007): 190-194.

Khani, Shahrokh C., et al. "AAV-mediated expression targeting of rod and cone photoreceptors with a human rhodopsin kinase promoter." Investigative ophthalmology & visual science 48.9 (2007): 3954-3961.

Koenekoop, Robert K. "An overview of Leber congenital amaurosis: a model to understand human retinal development." Survey of ophthalmology 49.4 (2004): 379-398.

Komáromy, András M., et al. "Gene therapy rescues cone function in congenital achromatopsia." Human molecular genetics 19.13 (2010): 2581-2593.

Kotterman et al., 2014, Nature Reviews, vol. 15, p. 445-451.

Kumaran, Neruban, et al. "Leber congenital amaurosis/early-onset severe retinal dystrophy: clinical features, molecular genetics and therapeutic interventions." British journal of ophthalmology 101.9 (2017): 1147-1154.

Kurth, Ingo, et al. "Targeted disruption of the murine retinal dehydrogenase gene Rdh12 does not limit visual cycle function." Molecular and cellular biology 27.4 (2007): 1370-1379.

Ebherz, Corinna, et al. "Novel AAV serotypes for improved ocular gene transfer." The Journal of Gene Medicine: A cross-disciplinary journal for research on the science of gene transfer and its clinical applications 10.4 (2008): 375-382.

Lee, Seung-Ah, Olga V. Belyaeva, and Natalia Y. Kedishvili. "Effect of lipid peroxidation products on the activity of human retinol dehydrogenase 12 (RDH12) and retinoid metabolism." Biochimica et Biophysica Acta (BBA)-Molecular Basis of Disease 1782.6 (2008): 421-425.

Enzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.

Lhériteau, Elsa, et al. "The RPGRIP1-deficient dog, a promising canine model for gene therapy." Molecular vision 15 (2009): 349-61.

Lopes, Vanda S., et al. "Dysfunction of heterotrimeric kinesin-2 in rod photoreceptor cells and the role of opsin mislocalization in rapid cell death." Molecular biology of the cell 21.23 (2010): 4076-4088.

Lotery, Andrew J., et al. "Adeno-associated virus type 5: transduction efficiency and cell-type specificity in the primate retina." Human gene therapy 14.17 (2003): 1663-1671.

Mackay, Donna S., et al. "RDH12 retinopathy: novel mutations and phenotypic description." Molecular vision 17 (2011): 2706.

MacKenzie, Donald, et al. "Localization of binding sites for carboxyl terminal specific anti-rhodopsin monoclonal antibodies using synthetic peptides." Biochemistry 23.26 (1984): 6544-6549.

MacLaren, Robert E., et al. "Retinal gene therapy in patients with choroideremia: initial findings from a phase ½ clinical trial." The Lancet 383.9923 (2014): 1129-1137.

Maeda, Akiko, et al. "Retinol dehydrogenase (RDH12) protects photoreceptors from light-induced degeneration in mice." Journal of Biological Chemistry 281.49 (2006): 37697-37704.

Maguire, Albert M., et al. "Safety and efficacy of gene transfer for Leber's congenital amaurosis." New England Journal of Medicine 358.21 (2008): 2240-2248.

Beltran et al., 2010, "rAAV2/5 gene-targeting to rods: dose-dependent efficiency and complications associated with different promoters", Gene Ther. Sep. 2010 ; 17(9): 1162-1174.

Fingert et al., 2008, "Association of a Novel Mutation in the Retinol Dehydrogenase 12 (RDG12) Genre with Autosomal Dominant Retinitis Pigmentosa", Arch Ophthalmol. 2008; 126(9):1301-1307.

(56) References Cited

OTHER PUBLICATIONS

Maqbool et al., 2015, Biochemical Society Transactions, vol. 43, No. 5, p. 1011-1017.

Marchette, Lea D., et al. "Retinol dehydrogenase 12 detoxifies 4-hydroxynonenal in photoreceptor cells." Free Radical Biology and Medicine 48.1 (2010): 16-25.

McLaughlin, Susan K., et al. "Adeno-associated virus general transduction vectors: analysis of proviral structures." Journal of virology 62.6 (1988): 1963-1973.

Muzyczka, N. "Use of adeno-associated virus as a general transduction vector for mammalian cells." Viral expression vectors (1992): 97-129.

Natkunarajah, M., et al. "Assessment of ocular transduction using single-stranded and self-complementary recombinant adeno-associated virus serotype ⅖." Gene therapy 15.6 (2008): 463-467.

Neitz et al., 2011, Geneseq Accession No. AZG67301, computer printout, pp. 1-2.

Nishiguchi, Koji M., et al. "Gene therapy restores vision in rd1 mice after removal of a confounding mutation in Gpr179." Nature communications 6.1 10 pages (2015): 6006.

Pang, J-J., et al. "AAV-mediated gene therapy in mouse models of recessive retinal degeneration." Current molecular medicine 12.3 (2012): 316-330.

Pawlyk, Basil S., et al. "Gene replacement therapy rescues photoreceptor degeneration in a murine model of Leber congenital amaurosis lacking RPGRIP." Investigative ophthalmology & visual science 46.9 (2005): 3039-3045.

Pawlyk, Basil S., et al. "Replacement gene therapy with a human RPGRIP1 sequence slows photoreceptor degeneration in a murine model of Leber congenital amaurosis." Human gene therapy 21.8 (2010): 993-1004.

Perrault, Isabelle, et al. "Retinal dehydrogenase 12 (RDH12) mutations in leber congenital amaurosis." The American Journal of Human Genetics 75.4 (2004): 639-646.

Peterson, Gary L. "A simplification of the protein assay method of Lowry et al. which is more generally applicable." Analytical biochemistry 83.2 (1977): 346-356.

Rattner, Amir, Philip M. Smallwood, and Jeremy Nathans. "Identification and characterization of all-trans-retinol dehydrogenase from photoreceptor outer segments, the visual cycle enzyme that reduces all-trans-retinal to all-trans-retinol." Journal of Biological Chemistry 275.15 (2000): 11034-11043.

Samulski, Richard Jude, Long-Sheng Chang, and T. Shenk. "Helper-free stocks of recombinant adeno-associated viruses: normal integration does not require viral gene expression." Journal of virology 63.9 (1989): 3822-3828.

Schuster, Andreas, et al. "The phenotype of early-onset retinal degeneration in persons with RDH12 mutations." Investigative ophthalmology & visual science 48.4 (2007): 1824-1831.

Shim et al., 2017, Current Gene Therapy, vol. 17, No. 5, p. 1-18.

Smith, Alexander J., James W. Bainbridge, and Robin R. Ali. "Prospects for retinal gene replacement therapy." Trends in Genetics 25.4 (2009): 156-165.

Sparrow, Janet R. "Bisretinoids of RPE lipofuscin: trigger for complement activation in age-related macular degeneration." Inflammation and Retinal Disease: Complement Biology and Pathology (2010): 63-74.

Sun, Xun, et al. "Gene therapy with a promoter targeting both rods and cones rescues retinal degeneration caused by AIPL1 mutations." Gene therapy 17.1 (2010): 117-131.

Tan, Mei Hong, et al. "Gene therapy for retinitis pigmentosa and Leber congenital amaurosis caused by defects in AIPL1: effective rescue of mouse models of partial and complete Aipl1 deficiency using AAV2/2 and AAV2/8 vectors." Human molecular genetics 18.12 (2009): 2099-2114.

Thompson et al., "AAV-mediated Expression of Human Rdh12 in Mouse Retina," ARVO Annual Meeting Abstract (2012).

Thompson, Debra A., and Andreas Gal. "Vitamin A metabolism in the retinal pigment epithelium: genes, mutations, and diseases." Progress in retinal and eye research 22.5 (2003): 683-703.

Thompson, Debra A., et al. "Rd9 is a naturally occurring mouse model of a common form of retinitis pigmentosa caused by mutations in RPGR-ORF15." PloS one 7.5 (2012): e35865.

Thompson, Debra A., et al. "Retinal degeneration associated with RDH12 mutations results from decreased 11-cis retinal synthesis due to disruption of the visual cycle." Human molecular genetics 14.24 (2005): 3865-3875.

Tratschin, J. D., Irving L. Miller, and Barrie J. Carter. "Genetic analysis of adeno-associated virus: properties of deletion mutants constructed in vitro and evidence for an adeno-associated virus replication function." Journal of Virology 51.3 (1984): 611-619.

Tratschin, Jon-Duri, et al. "A human parvovirus, adeno-associated virus, as a eucaryotic vector: transient expression and encapsidation of the procaryotic gene for chloramphenicol acetyltransferase." Molecular and cellular biology 4.10 (1984): 2072-2081.

Tratschin, Jon-Duri, et al. "Adeno-associated virus vector for high-frequency integration, expression, and rescue of genes in mammalian cells." Molecular and Cellular Biology 5.11 (1985): 3251-3260.

Turney, Clare, et al. "Pathological and electrophysiological features of a canine cone-rod dystrophy in the miniature longhaired dachshund." Investigative ophthalmology & visual science 48.9 (2007): 4240-4249.

Vandenberghe, Luk H., et al. "AAV9 targets cone photoreceptors in the nonhuman primate retina." PloS one 8.1 (2013): e53463.

Vandenberghe, Luk H., et al. "Dosage thresholds for AAV2 and AAV8 photoreceptor gene therapy in monkey." Science translational medicine 3.88 (2011): 88ra54-88ra54.

Weleber et al., "Leber Congenital Amaurosis", 32 pages (2004).

Wondisford et al., "Cloning Of The Human Thyrotropin Beta-Subunit Gene And Transient Expression Of Biologically Active Human Thyrotropin After Gene Transfection," Mol Endocrinol 2:32-9 (1988).

Xiao et al., "Production Of High-Titer Recombinant Adena-Associated Virus Vectors In The Absence Of Helper Adenovirus," J Viral 72:2224-32 (1998).

Yang et al., "Virus-Mediated Transduction Of Murine Retina With Adena-Associated Virus: Effects Of Viral Capsid And Genome Size," J Viral 76(15):7651-60 (2002).

Young et al., "A Short, Highly Active Photoreceptor-Specific Enhancer/Promoter Region Upstream Of The Human Rhodopsin Kinase Gene," Invest Ophthalmol Vis Sci 44(9):4076-85 (2003).

Daich Varela et al. "Leber congenital amaurosis/early-onset severe retinal dystrophy: current management and clinical trials." British Journal of Ophthalmology, 2022; 106:445-451.

Kim et al. "Codon optimization for high-level expression of human erythropoietin (EPO) in mammalian cells." Gene, vol. 199 (1997), p. 293-301.

Zou et al., "Phenotypic Variability of Recessive RDH12-Associated Retinal Dystrophy," Retina. Oct. 2019;39(10): 2040-2052, doi: 10.1097/IAE.0000000000002242, 1 page.

Communication pursuant to Rule 114(2) EPC (third party observations) for EP 11878835.0 dated Dec. 20, 2022, 16 pages.

Retinal Health Series-Leber Congenial Amaurosis, 2 pages (2018).

Sun Wenyu et al., "Novel RDH12 mutations associated with Leber congenital amaurosis and cone-rod dystrophy: Biochemical and clinical evaluations." Vision Res. Jul. 2007, vol. 47, N. 15, pp. 2055-2066.

Auricchio, A. Pseudotyped AAV vectors for constitutive and regulated gene expression in the eye. Vision Res. Apr. 2003;43(8):913-8.

Kim, S.J. Novel Approaches for Retinal Drug and Gene Delivery. TVST 3(5): article 7, 10 pages, 2014.

Kumaran, Leber Congenital Amaurosis / Early-Onset Severe Retinal Dystrophy Overview. Retrieved on-line https://www.ncbi.nlm.nih.gov/books/NBK531510/. Initial Posting: Oct. 4, 2018; Last Revision: Mar. 23, 2023, 18 pages.

Mauro, V. P. et al. A critical analysis of codon optimization in human therapeutics. Trends Mol Med. Nov. 2014 ; 20(11): 604-613.

Rowe-Rendleman, C. L. et al. Drug and Gene Delivery to the Back of the Eye: From Bench to Bedside. Invest Ophthalmol Vis Sci. 2014;55:2714-2730.

Sarkar, H. and Moosajee, M. Retinol dehydrogenase 12 (RDH12): Role in vision, retinal disease and future perspectives. Experimental Eye Research 188 (2019) 107793.

(56) References Cited

OTHER PUBLICATIONS

Sarkar, H. et al. Novel Heterozygous Deletion in Retinol Dehydrogenase 12 (RDH12) Causes Familial Autosomal Dominant Retinitis Pigmentosa. Frontiers in Genetics, Apr. 2020 | vol. 11 | Article 335, 6 pages.

Sofia, F. et al. Report from a Workshop on Accelerating the Development of Treatments for Inherited Retinal Dystrophies Associated with Mutations in the RDH12 Gene. TVST 9(8): article 30, 7 pages, Jul. 17, 2020.

Tuohy, G. A report on a workshop for acceleratingthe development of treatments forinherited retinal degenerations (IRDs). Published on Sep. 9, 2020, 3 pages.

* cited by examiner

SEQUENCE LISTING

```
Sequence total quantity: 5
SEQ ID NO: 1              moltype = DNA  length = 990
FEATURE                  Location/Qualifiers
source                   1..990
                         mol_type = genomic DNA
                         organism = Homo sapiens
SEQUENCE: 1
agttggaacg atgctggtca ccttgggact gctcacctcc ttcttctcgt tcctgtatat  60
ggtagctcca tccatcagga agttctttgc tggtggagtg tgtagaacaa atgtgcagct  120
tcctggcaag gtagtggtga tcactggcgc caacacgggc attggcaagg agacggccag  180
agagctcgct agccgaggag cccgagtcta tattgcctgc agagatgtac tgaaggggga  240
gtctgctgcc agtgaaatcc gagtggatac aaagaactcc caggtgctgg tgcggaaatt  300
ggacctatcc gacaccaaat ctatccgagc ctttgctgag ggctttctgg cagaggaaaa  360
gcagctccat attctgatca acaatgcggg agtaatgatg tgtccatatt ccaagacagc  420
tgatggcttt gaaacccacc tgggagtcaa ccacctgggc cacttcctcc tcacctacct  480
gctcctggag cggctaaagg tgtctgcccc tgcacgggtg gttaatgtgt cctcggtggc  540
tcaccacatt ggcaagattc ccttccacga cctccagagc gagaagcgct acagcagggg  600
ttttgcctat tgccacagca agctggccaa tgtgcttttt actcgtgagc tggccaagag  660
gctccaaggc accggggtca ccacctacgc agtgcaccca ggcgtcgtcc gctctgagct  720
ggtccggcac tcctccctgc tctgcctgct ctggcggctc ttctcccct ttgtcaagac  780
ggcacgggag ggggcgcaga ccagcctgca ctgcgccctg gctgagggcc tggagcccct  840
gagtggcaag tacttcagtg actgcaagag gacctgggtg tctccaaggg cccgaaataa  900
caaaacagct gagcgcctat ggaatgtcag ctgtgagctt ctaggaatcc ggtgggagta  960
gctggtggaa gagctgcagc tttatcaggc                                   990

SEQ ID NO: 2              moltype = AA  length = 316
FEATURE                  Location/Qualifiers
source                   1..316
                         mol_type = protein
                         organism = Homo sapiens
SEQUENCE: 2
MLVTLGLLTS FFSFLYMVAP SIRKFFAGGV CRTNVQLPGK VVVITGANTG IGKETARELA  60
SRGARVYIAC RDVLKGESAA SEIRVDTKNS QVLVRKLDLS DTKSIRAFAE GFLAEEKQLH  120
ILINNAGVMM CPYSKTADGF ETHLGVNHLG HFLLTYLLLE RLKVSAPARV VNVSSVAHHI  180
GKIPFHDLQS EKRYSRGFAY CHSKLANVLF TRELAKRLQG TGVTTYAVHP GVVRSELVRH  240
SSLLCLLWRL FSPFVKTARE GAQTSLHCAL AEGLEPLSGK YFSDCKRTWV SPRARNNKTA  300
ERLWNVSCEL LGIRWE                                                   316

SEQ ID NO: 3              moltype = DNA  length = 199
FEATURE                  Location/Qualifiers
source                   1..199
                         mol_type = genomic DNA
                         organism = Homo sapiens
SEQUENCE: 3
gggcccagga agcctggtgg ttgtttgtcc ttctcagggg aaaagtgagg cggcccttg   60
gaggaagggg ccgggcagaa tgatctaatc ggattccaag cagctcaggg gattgtcttt  120
ttctagcacc ttcttgccac tcctaagcgt cctccgtgac cccggctggg atttagcctg  180
gtgctgtgtc agccccggt                                               199

SEQ ID NO: 4              moltype = AA  length = 12
FEATURE                  Location/Qualifiers
source                   1..12
                         mol_type = protein
                         organism = Mus musculus
SEQUENCE: 4
SPFFKSTSQG AQ                                                       12

SEQ ID NO: 5              moltype = AA  length = 16
FEATURE                  Location/Qualifiers
source                   1..16
                         mol_type = protein
                         organism = Homo sapiens
SEQUENCE: 5
DCKRTWVSPR ARNNKT                                                   16
```

VIRAL VECTORS COMPRISING RDH12 CODING REGIONS AND METHODS OF TREATING RETINAL DYSTROPHIES

CROSS-REFERENCE TO RELATED APPLICATIONS

This application is a Continuation of U.S. patent application Ser. No. 16/192,382, filed Nov. 15, 2018, which claims the priority benefit of provisional U.S. Patent Application No. 62/586,624, filed Nov. 15, 2017, the entireties of each of which are incorporated herein by reference.

INCORPORATION BY REFERENCE OF MATERIALS SUBMITTED ELECTRONICALLY

This application contains, as a separate part of the disclosure, a Sequence Listing submitted electronically in XML format (filename: 2960447-000004-US1_SL.XML; created Feb. 12, 2023; 6,933 in size), which is incorporated herein by reference in its entirety.

FIELD

The disclosure relates to medical treatment methods, such as methods for treating a human subject with an ophthalmological condition, e.g., Leber congenital amaurosis, due to at least one loss-of-function mutation in the gene encoding the Retinol Dehydrogenase 12 protein (RDH12), the method comprising administering to the subject an effective amount of a nucleic acid comprising an adeno-associated viral vector comprising a human RDH12 complementary DNA (cDNA).

BACKGROUND

Inherited retinal disease (IRD) is a leading cause of legal blindness in children. Leber congenital amaurosis (LCA) and early-onset severe retinal dystrophy (EOSRD) result in severe visual impairment beginning at birth to a few years of age, and together account for 5% or more of all IRD (Koenekoop et al. 2004). LCA/EOSRD is associated with autosomal dominant and autosomal recessive modes of inheritance, involving the retinal pigment epithelium and the rod and cone photoreceptors as primary targets (Weleber et al. 2013). Approximately 10% of LCA/EOSRD is caused by mutations in the gene encoding RDH12 (Kumaran et al. 2017). Given the role of RDH12 in the visual cycle that provides chromophore to the photoreceptor cells (Haeseleer et al. 2002; Chen et al. 2012), and which constitutes a critical therapeutic target, RDH12 is one of the most important LCA genes.

Despite the prevalence of ophthalmological conditions such as inherited retinal disease in humans and non-human mammals, and knowledge of genes encoding retinol dehydrogenases as well as the effect some mutations in those genes have, there is no known treatment for LCA caused by one or more mutations in RDH12. Accordingly, a need continues to exist in the art for materials and methods useful in treating retinal dystrophies such as LCA as well as materials and methods useful in correcting genetic anomalies that can lead to such dystrophies.

SUMMARY

The invention provides an adeno-associated virus (AAV) vector comprising a coding region for the gene product of the RDH12 gene, a gene encoding a retinol dehydrogenase enzyme. The AAV vector comprising RDH12 is useful in treating retinal dystrophy disorders such as Leber Congenital Amaurosis (LCA) by providing a recombinant construct in which an RDH12 coding region is placed under the control of a regulable, or controllable, promoter, such as a heterologous promoter, to provide complementing retinol dehydrogenase to subjects lacking wild-type levels of RDH12 activity, such as would result from mutations in RDH12. Despite the advantages of relatively small genome size, relatively low tendency to integrate into host DNA, and relatively low immunogenic profile, a surprising finding has been that some AAV serotype combinations, or pseudotypes, yield expression levels for encoded RDH12 product that is not therapeutically effective and/or that exhibits undesirable toxicity in the context of administration to subjects to treat retinal dystrophies. Coincident with that finding is the finding that certain pseudotypes, such as the AAV2/5 pseudotype, demonstrate unexpected and surprisingly effective expression levels and toxicity profiles compatible with therapeutic use to treat retinal dystrophies. Subjects who can be treated by the present methods can include those who have loss of visual function (e.g., impaired response on electroretinogram (ERG) testing), but who retain some photoreceptor cells as determined by optical coherence tomography (OCT). Thus, in one aspect, the disclosure provides a method of treating a human subject who has an ophthalmological condition, such as Leber Congenital Amaurosis, or LCA, or another clinically defined ophthalmological condition due to one or more loss-of-function mutations in the gene encoding the Retinol Dehydrogenase12 (RDH12) protein. More particularly, one aspect of the disclosure provides a method of treating a human subject who has an ophthalmological condition due to one or more loss-of-function mutations in the gene encoding the Retinol Dehydrogenase 12 (RDH12) protein, the method comprising administering to at least one eye of the subject an adeno-associated viral vector comprising a nucleic acid, wherein the nucleic acid comprises human RDH12 DNA, e.g., human RDH12 cDNA, and wherein the RDH12 DNA (e.g., human RDH12 DNA) encodes a protein that is at least 70%, 80%, 90%, 95%, or 99% identical to the full length of SEQ ID NO:2. In some embodiments, the ophthalmological condition is Leber Congenital Amaurosis (LCA). In some embodiments, the RDH12 DNA, e.g., RDH12 cDNA, is under the expression control of a human rhodopsin kinase 1 (hGRK1) promoter, such as wherein the hGRK1 promoter comprises or consists essentially of SEQ ID NO:3. In some embodiments, the adeno-associated viral vector is AAV-2, serotype-5 (AAV2/5) or AAV-5. In some embodiments, the RDH12 DNA, e.g., RDH12 cDNA, comprises a sequence that is at least 60% or 70% identical to SEQ ID NO:1. In some embodiments, the nucleic acid is administered at a titer of about $2\times10^{10}$ viral genomes per milliliter (vg/mL) to about $2\times10^{12}$ vg/mL, e.g., a titer of about $2\times10^{10}$ viral genomes per milliliter (vg/mL), about $2\times10^{11}$ vg/mL, or about $2\times10^{12}$ vg/mL. In some embodiments, the nucleic acid is administered into the subretinal space.

Another aspect of the disclosure is drawn to a nucleic acid encoding a human RDH12 DNA, e.g., a human RDH12 cDNA, wherein the human RDH12 DNA encodes a protein that is at least 70%, 80%, 90%, 95%, or 99% identical to the full length of SEQ ID NO:2, wherein the RDH12 DNA is under the control of a human rhodopsin kinase 1 (hGRK1) promoter. In some embodiments, the hGRK1 promoter comprises or consists essentially of SEQ ID NO:3. In some embodiments, the human RDH12 DNA, e.g., RDH12 cDNA, encodes a protein comprising SEQ ID NO:2. In some embodiments, the human RDH12 DNA, e.g., RDH12 cDNA, is at least 60% or 70% identical to the full length of SEQ ID NO: 1.

Yet another aspect of the disclosure is a nucleic acid as disclosed herein for use in treating a human subject who has an ophthalmological condition due to one or more loss-of-function mutations in the gene encoding the Retinol Dehydrogenase 12 (RDH12) protein. In some embodiments, the ophthalmological condition is Leber Congenital Amaurosis (LCA).

Still another aspect of the disclosure is a viral vector comprising a nucleic acid encoding RDH12 as disclosed herein. In some embodiments, the viral vector is an adeno-associated viral vector. In some embodiments, the adeno-associated viral vector is AAV-2, serotype-5 (AAV2/5) or AAV-5.

Another aspect of the disclosure is a viral vector as disclosed herein for use in treating a human subject who has an ophthalmological condition due to one or more loss-of-function mutations in the gene encoding the Retinol Dehydrogenase 12 (RDH12) protein. In some embodiments, the ophthalmological condition is Leber Congenital Amaurosis (LCA).

Another aspect of the disclosure is directed to an isolated host cell comprising a viral vector as disclosed herein, or a nucleic acid as disclosed herein. In some embodiments, the isolated host cell expresses a human RDH12 protein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

5

6 injected; and Rdh12$^{-/-}$ AAV2/5-hGRK1p.hRDH12 injected mice (up to 2×10$^9$ vg). ERGs from a representative animal in each treatment group measured at 6 weeks post-injection are shown.

Figure 2:
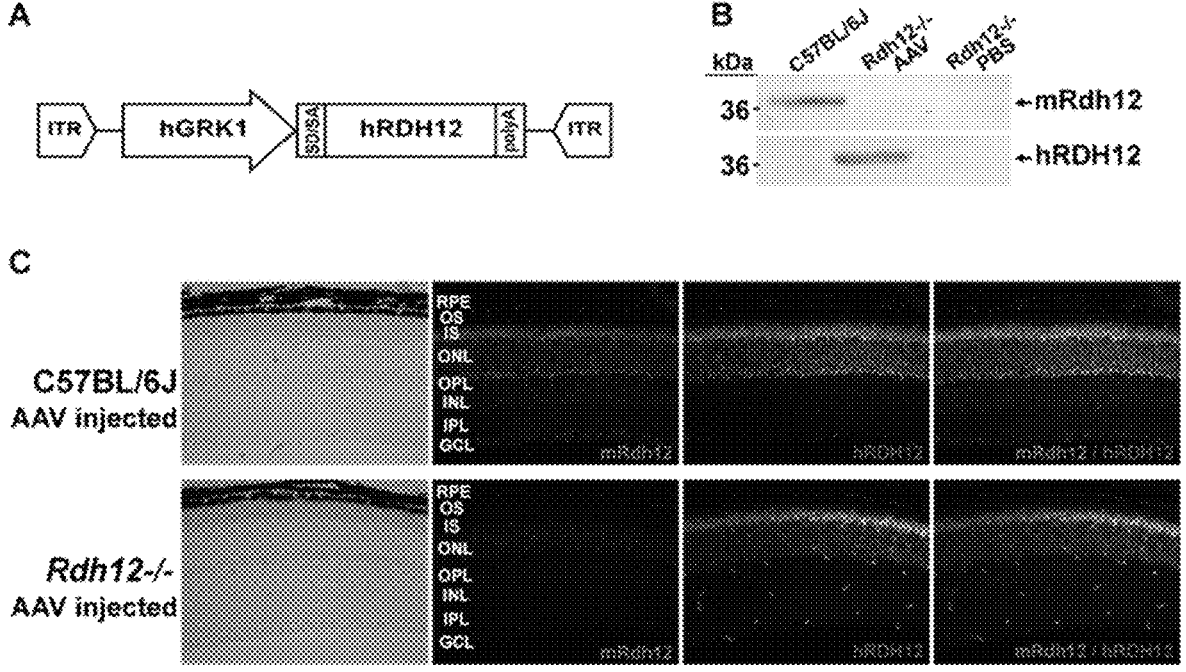
FIG. 2. Expression and localization of recombinant RDH12 in AAV2/5-hGRK1p.hRDH12 injected mice. (A) Schematic of the AAV2/5-hGRK1p.hRDH12 gene-therapy construct in which a human RDH12 cDNA is cloned downstream of a human rhodopsin kinase promoter, between inverted terminal repeat sequences derived from the AAV2 genome. (B, C) Expression of human RDH12 protein in mouse retinas at 6 weeks following sub-retinal injection of AAV2/5-hGRK1p.hRDH12 ($1.3 \times 10^9$ vg) or PBS, evaluated using antibodies specific for mouse Rdh12 or human RDH12. (B) Western analysis of retinal lysates from C57BL/6J mice, PBS injected Rdh12$^{-/-}$ mice, and AAV2/5-hGRK1p.hRDH12-injected Rdh12$^{-/-}$ mice. (C) Immuno-histochemical analysis shows localization of native mouse Rdh12 (dark gray) to the IS, ONL, and OPL of the retina in C57BL/6J mice but not in Rdh12$^{-/-}$ mice, whereas recombinant human RDH12 (light gray) resulting from injection of AAV2/5-hGRK1p.hRDH12 shows similar localization both C57BL/6J and Rdh12$^{-/-}$ mice. Phase contrast images (left). Abbreviations: ITR, inverted terminal repeat; hGRK1, human rhodopsin kinase promoter; SD/SA, Simian virus 40 splice donor/splice acceptor site; hRDH12, human RDH12 cDNA; polyA, Simian virus 40 polyadenylation signal; RPE, retinal pigment epithelium; OS, outer segments; IS, inner segments; ONL, outer nuclear layer; OPL, outer plexiform layer; INL, inner nuclear layer; IPL, inner plexiform layer; GCL, ganglion cell layer.
Figure 7:
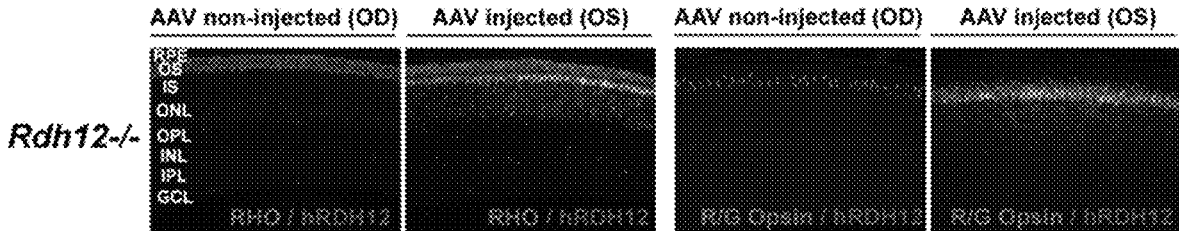

FIG. 7. Visual pigment localization is not perturbed by AAV2/5-hGRK1p.hRDH12. Immunohistochemical localization of rhodopsin and cone opsin in non-injected and injected (1.3×10$^9$ vg)Rdh12$^{-/-}$ mice evaluated at 16 weeks post treatment. Human RDH12 protein expression in IS and ONL (light gray). Rhodopsin and red/green opsin (dark gray) in AAV2/5-hGRK1p.hRDH12 injected eyes. Abbreviations are as described for FIG. 2.

Figure 8:
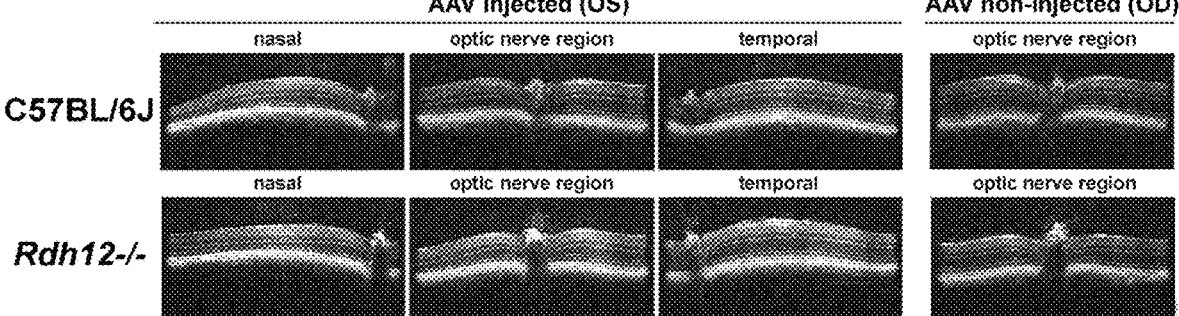

FIG. 8. Retinal structure is not damaged by long-term expression of AAV2/5-hGRK1p.hRDH12. Optical coherence tomography (OCT) analysis of eyes of C57BL/6J and Rdh12"$^1$" mice evaluated at 54 weeks post injection of AAV2/5-hGRK1p.hRDH12 (up to 2×10$^9$ vg).

Figure 9:
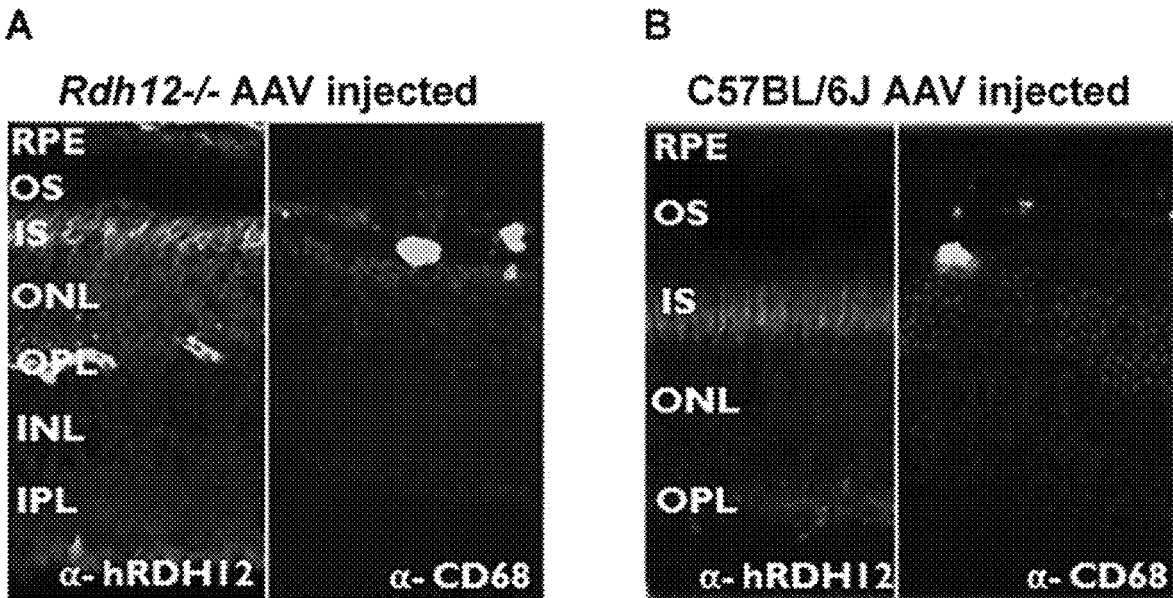

FIG. 9. Infiltrating CD68+ macrophages and RDH12 expression in AAV2/8-hGRK1p.hRDH12 injected retinas. Rdh12$^{-/-}$ and C57BL/6J mice evaluated by immunohistochemical analysis 8 weeks following subretinal injection of AAV2/8-hGRK1p.hRDH12 (2×10$^9$ vg). Human RDH12 expression in IS, ONL, and OPL (light gray) and CD68 labeling of macrophages (white). Abbreviations are as described for FIG. 2.

DETAILED DESCRIPTION

Inherited retinal degeneration is a rare cause of profound vision loss that is a focus of current efforts to develop targeted gene-therapy. Viral vector-mediated somatic gene therapy has shown great promise in treating animal models of human retinal degenerative disease. To date, there have been a number of successful studies using adeno-associated virus (AAV)-mediated gene delivery to rescue photoreceptor degeneration in small animal models (Ali et al. 2000; Pang et al. 2012; Pawlyk et al. 2010; Pawlyk et al. 2005; Tan et al. 2009) and large animal models (Acland et al. 2001; Alexander et al. 2007; Beltran et al. 2012; Komaromy et al. 2010; Lheriteau et al. 2009). In these cases, the retinal pigment epithelium (RPE) or photoreceptors have been the primary targets for transgene expression. In addition, phase I clinical trials involving gene therapy for patients with Leber Congenital Amaurosis (LCA) targeting the RPE (Bainbridge et al. 2008; Cideciyan et al. 2008; Maguire et al. 2008) and more recently choroideremia (Maclaren et al. 2014), have already met with some success. There are currently no clinical trials using AAV-mediated gene replacement therapy for the treatment of patients with inherited retinal degeneration caused by mutations in RDH12.

With an interest in developing AAV-mediated gene therapy for the treatment of individuals with mutations in RDH12, we generated adeno-associated virus vectors carrying human RDH12 cDNA in which expression is under the control of a rhodopsin-kinase promoter. In the disclosed study of vectors with capsids derived from AAV serotype 5 or AAV serotype 8, we have shown that subretinal delivery of AAV2/5-hGRK1p.RDH12 in Rdh12-deficient (Rdh12$^{-/-}$) mice results in expression of recombinant human RDH12 that is stable, correctly localized, reconstitutes retinal reductase activity, reduces light-damage susceptibility, and does not cause the retinal toxicity seen with AAV2/8-hGRK1p.hRDH12. This AAV2/5-hGRK1p.RDH12 construct provides a product for RDH12 gene-replacement therapy.

RDH12

Figure 1:
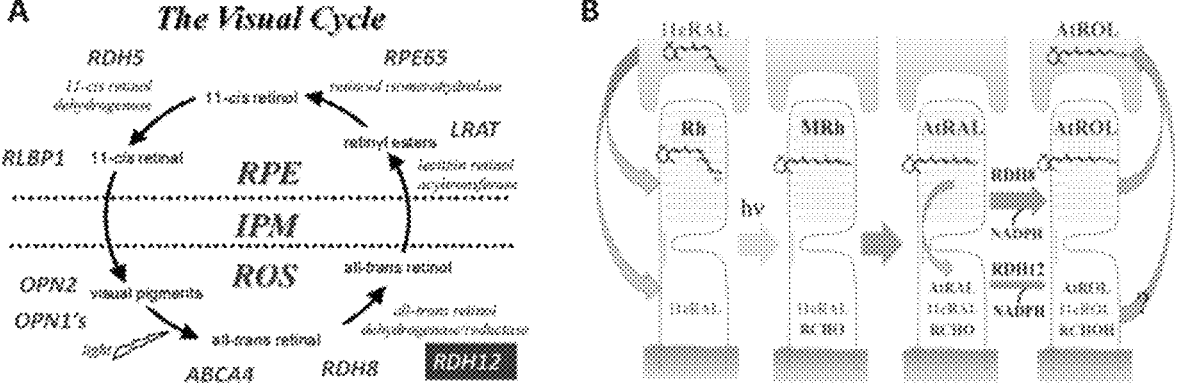
FIG. 1. RDH activity in the visual cycle and photoreceptor cells. (A) The visual cycle converts vitamin A to 11-cis retinal, the chromophore of the visual pigments, and recycles all-trans retinal released after bleaching. (B) Retinoid flow shown for a RPE-photoreceptor cell pair. RDH8 in the outer segment can reduce all-trans retinal. RDH12 in the inner segment can reduce all-trans retinal, 11-cis retinal, and other toxic short chain aldehydes. Abbreviations: 11cRAL, 11-cis retinal; 11cROL, 11-cis retinol; AtRAL, all-trans retinal; AtROL, all-trans retinol; RCHO, short-chain aldehyde; RCHOH, short-chain alcohol; Rh, rhodopsin; MRh, metarhodopsin.

Mutations in the gene encoding retinol dehydrogenase 12 (RDH12) cause severe early-onset retinal degeneration most often diagnosed as Leber congenital amaurosis (LCA) or early-onset severe retinal dystrophy (EOSRD). A member of the family of short-chain dehydrogenases/reductases, RDH12 is essential for reducing retinaldehydes that are generated by the activity of the vitamin A visual cycle that is integral to the light response of the photoreceptor cells. When visual pigments containing the 11-cis retinal chromophore absorb a photon of light, 11-cis retinal is isomerized to all-trans retinal, thus initiating a signal transduction cascade that regulates synaptic signaling. Visual pigment inactivation involves release of all-trans retinal, its reduction to all-trans retinol and return to the retinal pigment epithelium (RPE) for regeneration of the 11-cis retinal chromophore (FIG. 1A). When these recycling reactions are inefficient or disrupted, e.g., by aging or inherited disease, retinaldehydes and retinaldehyde-condensation products accumulate in the photoreceptors and retinal pigment epithelium, resulting in profound damage to the outer retina (Ben-Shabat et al. 2001; Thompson et al. 2003; Sparrow, 2010; Chen et al. 2012).

To protect against toxicity, a number of retinoid binding proteins and enzymes are expressed in the retina. RDH12 is a member of the family of short-chain dehydrogenases/reductases that uses NADPH to reduce a broad range of substrates, including cis- and trans-retinaldehydes (Haeseleer et al. 2002), C9 aldehydes generated as a result of lipid photo-oxidation (Belyaeva et al. 2005; Lee et al. 2008; Marchette et al. 2010), and steroid substrates (Keller et al. 2007). Individuals with loss-of-function mutations in the RDH12 gene exhibit a severe retinal degeneration phenotype often diagnosed as Leber congenital amaurosis (LCA) (Janecke et al. 2004; Thompson et al. 2005; Perrault et al. 2004; den Hollander et al. 2008; Mackay et al. 2011), for which there is currently no treatments or cures. RDH12 localizes to the inner segments of rod and cone photoreceptor cells (Haeseleer et al. 2002; Maeda et al. 2006) where it protects against light-induced damage caused, at least in part, by reactive retinaldehydes (Maeda et al. 2006). All-trans retinal generated after light exposure has been shown to leak from photoreceptor outer segments to inner segments, and its effective clearance from photoreceptor cells requires the activity of both RDH8 present in the outer segments, and RDH12 present in the inner segments (Chen et al. 2012) (FIG. 1B). As such, RDH12 also has the potential to play an important role in reducing 11-cis retinal present in excess of that required for opsin biosynthesis, which can enter the inner segment from the subretinal space (Chen et al. 2012).

To investigate the potential of gene replacement therapy for LCA/EOSRD due to RDH12 mutations, we generated adeno-associated virus vectors carrying a human RDH12 cDNA, in which expression is under the control of a rhodopsin-kinase promoter that directs photoreceptor-cell specific expression (Khani et al. 2007; Sun et al. 2010; Young et al. 2003). The DNA construct was packaged with a capsid derived from AAV serotype 8 that mediates efficient and robust transduction of photoreceptor cells (Allocca et al. 2007; Natkunarajah et al. 2008; Vandenberghe et al. 2011; Vandenberghe et al. 2013), or with a AAV serotype 5 capsid that mediates photoreceptor transduction, but with slower kinetics and less robust expression compared to the AAV serotype 8 capsid (Yang et al. 2002; Lotery et al. 2003; Allocca et al. 2007; Lebherz et al. 2008).

In comparative studies performed in a mouse model of Rdh12-deficiency (Rdh12$^{-/-}$) (Kurth et al. 2007), our work has shown that the two vectors have significantly different safety profiles, with AAV2/5-hGRK1p.hRDH12 demonstrating unexpected and surprisingly effective expression levels and toxicity profiles compatible with therapeutic use to treat retinal dystrophies.

Human RDH12 Sequence

Sequence of an exemplary human RDH12 cDNA, consisting of nucleotides −10 to +980 relative to the translation initiation site, encoding all seven translated RDH12 exons (GenBank #NM_152443) is provided in SEQ ID NO:1.

The full-length human RDH12 protein sequence is provided in SEQ ID NO:2.

Rhodopsin Kinase Promoter (hGRK1p)

In some embodiments of the methods described herein, a replacement gene construct is used in which a human RDH12 cDNA as described herein is placed under the control of a human rhodopsin kinase (hGRK1) promoter. In some embodiments, the hGRK1 promoter is approximately 200 base pairs (bp) in length containing a short promoter derived from the rhodopsin kinase (RK) hGRK1 gene, which has been shown to drive cell-specific expression in rods and cones (Khani et al. 2007; Sun et al. 2010; Young et al. 2003). An exemplary hGRK1 promoter sequence contains nucleotides −112 to +87 of SEQ ID NO:3 (Khani et al. 2007).

Viral Delivery Vector

The abbreviated human RDH12 cDNA, as described above, is packaged into a delivery vector, e.g., an AAV5 or AAV2/5 vector.

Replacement genes (cDNA) can be administered in any effective carrier, e.g., any formulation or composition capable of effectively delivering the component gene to cells in vivo. Approaches include insertion of the gene into non-pathogenic, non-replicating viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), poly lysine conjugates, gramacidin S, artificial viral envelopes or other such intracellular carriers, as well as direct injection of the gene construct or $Ca_3(PO_4)_2$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid. Retrovirus vectors and adenovirus derived vectors can be used as a recombinant gene delivery system for the transfer of exogenous genes in vivo, particularly into humans, in a number of cell types. However, they do not transduce the photoreceptor cells with sufficient efficiency to make them useful for this application.

Yet another viral vector system useful for delivery of nucleic acids is the adeno-associated virus (AAV). Adenoassociated virus is a naturally occurring defective virus that requires another virus, such as an adenovirus or a herpes virus, as a helper virus for efficient replication and a productive life cycle (Muzyczka et al. 1992). It is also one of the few viruses that may integrate its DNA into non-dividing cells, and exhibits a high frequency of stable integration (see, for example, Flotte et al. 1992; Samulski et al. 1989; and McLaughlin et al. 1988). Vectors containing as little as 300 base pairs of AAV can be packaged and can integrate. Space for exogenous DNA is limited to about 4.5 kb. An AAV vector such as that described in Tratschin et al., 1985 can be used to introduce DNA into cells. A variety of nucleic acids have been introduced into different cell types using AAV vectors (see, for example, Hermonat et al. 1984; Tratschin et al. 1984a; Tratschin et al. 1984b; Wondisford et al. 1988; and Flotte et al. 1993).

In preferred embodiments, the viral delivery vector is a recombinant AAV2/5 virus. Prior to administration, the final product can undergo a series of ultrapurification steps to meet clinical grade criteria.

Subject Selection

Subjects who are candidates for the present methods of treatment include those who have a diagnosis of LCA caused by mutations in the gene encoding RDH12. Subjects suffering from other ophthalmological clinically-defined conditions caused by mutations in the gene encoding RDH12, e.g., early-onset retinitis pigmentosa, can also be treated using the methods described herein. A diagnosis of LCA or another ophthalmological condition caused by mutations in the gene encoding RDH12 can be made using methods known in the art.

The methods described herein can include identifying a subject, e.g., a child, adolescent, or young adult subject, who has LCA or another ophthalmological condition caused by one or more mutations in the gene encoding RDH12, or who is suspected of having LCA or another ophthalmological condition caused by one or more mutations in the gene encoding RDH12 (e.g., based on the presence of symptoms of the condition and no other obvious cause), and obtaining a sample comprising genomic DNA from the subject, detecting the presence of mutations in RDH12 using known molecular biological methods, and selecting a patient who has mutations in both RDH12 alleles that cause LCA or another condition. Symptoms of the condition include macular atrophy, foveal thinning and disruption of laminar architecture, resulting in early central vision loss and progression to LP vision. Visual fields are constricted at the earliest age measured, and ERG responses become unrecordable by early adulthood. Detecting mutations in RDH12 can include sequencing all or part of the RDH12 gene in a subject, and comparing the sequence to a reference sequence (e.g., GenBank Accession No. NG_008321.1) to detect a mutation. Frameshift mutations, truncation mutations, mutations that alter a conserved amino acid, mutations that affect transcript splicing, or mutations that affect a regulatory (e.g., promoter) region are considered to be mutations that can cause LCA or another ophthalmological condition as described herein; an alteration in function can be confirmed by expressing the mutant in vitro (e.g., in cultured cells), and assaying, e.g., enzymatic function. Exemplary mutations in the homozygous state include: Glu127X, Gln189X, Tyr226Cys, Ala269GlyfsX1, and Leu274Pro (all position references refer to the RDH12 protein sequence of SEQ ID NO:2). Exemplary mutations in the compound heterozygous state include: Thr49Met/Arg62X; Arg65X/Ala269GlyfsX1; His151D/Thr155Ile; His151D/Arg269GlyfsX1 (Janecke et al. 2004; Schuster et al. 2007). (Positions refer to the protein sequence of SEQ ID NO:2.)

Patients with LCA or another ophthalmological condition due to at least one RDH12 mutation that can be treated using a method described herein preferably retain some photoreceptors and visual function, e.g., as measured by standard visual function or field tests and/or Optical Coherence Tomography (OCT, e.g., Spectral Domain-OCT (SD-OCT)). The methods described herein can include identifying subjects who have been diagnosed with LCA or another ophthalmological condition due to at least one RDH12 mutation, who have at least one confirmed mutation in RDH12 that causes their condition, and testing their visual ability and detecting the presence of residual central photoreceptors.

EXAMPLES

The disclosed and claimed subject matter is further described in the following examples, which do not limit the scope of the invention described in the claims.

Materials and Methods

The following materials and methods were used in the experiments disclosed in the Examples set forth below.

Animals

The generation and analysis of Rdh12$^{-/-}$ mice have been described previously (Kurth et al. 2007). The Rdh12$^{-/-}$ mice used in this study were bred from sibling mating among nullizygous males and females maintained in our institutional animal facility. WT mice used in the study were C57BL/6 from The Jackson Laboratory (Wilmington, MA).

Transgenic mice of the following genotypes were used for the studies disclosed herein: Rdh12$^{-/-}$ mice on C57BL/6J background homozygous for the Rpe65-Met450 (M/M) variant (Kurth, 2007), and albino Rdh12$^{-/-}$ mice on BALB/c background homozygous for the Rpe65-Leu450 (L/L) variant (Chrispell, 2009), that were obtained by breeding. Mice were reared in a 12-hour (light)/12-hour (dark) cycle and were euthanized by $CO_2$ inhalation followed by bilateral pneumothorax.

Plasmid Construction and Production of Recombinant AAV2/5 and AAV2/8

Human RDH12 cDNA were amplified from human retinal cDNA by PCR using primers designed to encompass the entire RDH12 coding region, cloned, and sequenced to verify fidelity, as described previously (Janecke et al. 2004). To construct the AAV vectors, RDH12 cDNAs were inserted into the multiple cloning site of the parental pAAV-hGRK1-hrGFP vector. The resulting pAAV-hGRK1-Rdh12 vector was packaged into AAV. AAV2/5 and AAV2/8 pseudotyped vectors were generated by bipartite transfection: (1) AAV vector plasmid encoding the gene of interest, (2) AAV helper plasmid encoding AAV Rep proteins from serotype 2 and Cap proteins from either serotype 5 or serotype 8, and adenovirus helper functions into 293T cells. The transfection and purification were performed using a protocol as published (Nishiguchi et al 2015). Two days after transfection, cells were lysed by repeated freeze and thaw cycles. After initial clearing of cell debris, the nucleic acid component of the virus producer cells was removed by Benzonase treatment. The recombinant AAV vector particles were purified by affinity chromatography using a AVB matrix, washed in 1×PBS and concentrated to a volume of 100-150 ml using Vivaspin 4 (10 kDa) concentrators. Vectors were titered by qPCR amplification.

Subretinal Injections

Cohorts of mice at approximately 4 weeks of age were placed under general anesthesia with an intraperitoneal injection of ketamine (90 mg/kg)/xylazine (9 mg/kg). A 0.5% proparacaine solution was applied to the cornea as a topical anesthetic. Pupils were dilated with topical application of tropicamide (0.5%). Under an ophthalmic surgical microscope, a small incision was made through the cornea adjacent to the limbus using a 30-gauge needle. A 34-gauge blunt needle fitted to a Hamilton syringe was inserted through the incision behind the lens and pushed through the retina. All injections were made subretinally in a location within the nasal quadrant of the retina. Each eye received up to 2×10$^9$ vg AAV2/5-(hGRK1)-hRDH12 in up to a 2 μL volume. RDH12-encoding vector was administered separately to one eye of each mouse receiving treatment, and the contralateral eyes were uninjected. Fundus examination following the injection found more than 30% of the retina detached in most cases, confirming successful subretinal delivery.

Antibodies

Primary antibodies used were: a rabbit anti-Rdh12 polyclonal antibody (CSP) specific for the mouse protein (against 252SPFFKSTSQGAQ263, SEQ ID NO:4), and a mouse anti-RDH12 monoclonal antibody (2C9) specific for the human protein (against C-284DCK-RTWVSPRARNNKT299; SEQ ID NO:5) (Kurth et al. 2007); a mouse anti-RHO monoclonal antibody (1D4) (MacKenzie et al. 1984); a rabbit anti-RHO polyclonal antibody generated against the denatured protein; and a rabbit anti-red/green cone opsin polyclonal antibody (Millipore cat # AB5405).

Immunoblotting Analysis

Proteins in retina homogenates were separated by SDS-PAGE, transferred onto nitrocellulose membranes that were then blocked, incubated with primary antibody overnight, washed, incubated with alkaline phosphatase-conjugated secondary antibody, and developed using 5-bromo-4-chloro-3'-indolylphosphate p-toluidine and nitro-blue tetrazolium chloride.

Histology and Immunofluorescence

Mice were euthanized, eyes scored for orientation, then enucleated. For cryosections, lens and anterior segments were removed, eyes briefly fixed with 4% paraformaldehyde, washed with PBS, transitioned to sucrose/OCT, flash-frozen, and sectioned at a thickness of 10 μm. For freeze-substitution preparation, whole eyes were flash-frozen in dry-ice-cooled isopentane for 30 seconds, and then transferred to dry-ice-cooled methanol containing 3% glacial acetic acid. Eyes were incubated at 80° C. for 48 hours, then overnight at −20° C., embedded in paraffin, and sectioned at a thickness of 6 μm. Paraffin sections were de-paraffinized and antigens retrieved by incubating in 1 mM EDTA, 0.05% Tween 20, pH8.0, at 90° C. for 30 minutes prior to immune labeling as follows. Briefly, retinal cross sections were washed with PBS and permeabilized with PBS-T (0.3% Triton X-100); blocked with 1% bovine serum albumin, 10% normal goat serum, and 0.3% Triton X-100; and incubated with primary antibodies overnight at 4° C., washed, then incubated with fluorophore-conjugated secondary antibodies for 1 hour at room temperature. Sections were cover-slipped using ProLong Gold gel mount containing 4',6-diamidino-2-phenylindole (DAPI; Invitrogen), and imaged using a Leica DM6000 fluorescence microscope.

ERG Recording

ERGs were performed as described previously (Thompson, 2012) using the Espion e2 recording system (Diagnosys, Lowell, MA). Briefly, mice were dark-adapted overnight and anesthetized with an intra-peritoneal injection of Ketamine (93 mg/kg) and Xylazine (8 mg/kg). Pupils were dilated with topical tropicamide (0.5%). Body temperature was maintained at 37° C. with a heating pad. Corneal ERGs were recorded from both eyes using gold wire loops with 0.5% tetracaine topical anesthesia and a drop of 2% methylcellulose for corneal hydration. A gold wire loop placed in the mouth was used as reference, and a ground electrode was on the tail. The ERG protocol consisted of recording dark-adapted (scotopic) responses to brief white flashes ($-2.31$ log cd·s·m$^{-2}$ for rod isolated B-waves; 1.09 log cd·s·m$^{-2}$ for rod-cone combined A- and B-waves). Light-adapted (photopic) ERGs were recorded after 10 minutes of adaptation to a white 32 cd·m$^{-2}$ rod-suppressing background in response to 1.09 log cd·s·m$^{-2}$ intensity flashes (for cone isolated B-waves). Responses were amplified at 1,000 gain at 1.25 to 1000 Hz, and digitized at a rate of 2000 Hz. A notch filter was used to remove 60 Hz line noise. Responses were computer-averaged and recorded at 3- to 60-second intervals depending upon the stimulus intensity. For statistical analysis, paired t-tests were used to determine if ERG amplitudes in treated eyes were significantly different from untreated eyes.

Analysis of Light-Induced Damage

Albino Rdh12$^{-/-}$ mice were injected in one eye with AAV2/5-hGRK1p.hRDH12 ($1.3\times10^9$ vg), or with an equal volume of PBS, and contralateral eyes were uninjected. At 6 weeks post-injection, ERG analysis was performed and scotopic responses were quantified as described above. One week later, mice were dark-adapted overnight, their pupils were dilated with tropicamide (0.5%), and then were placed in a light-box in individual clear trays. The mice were exposed to 5,000 lux for 2 hours, and then were returned to vivarium housing (12-hour dark/12-hour light ($<20$ lux)) for 7 days, after which ERG analysis was repeated. The percent of the original ERG response remaining after light damage was calculated for each eye, and the averages plotted with standard errors shown. Two-tailed paired t-tests were used to determine if the ERG amplitudes in treated eyes were significantly different from untreated eyes.

Optical Coherence Tomography

Mice were anesthetized and pupils dilated with 0.5% tropicamide. A spectral domain optical coherence tomography (OCT) system (Bioptigen Envisu R2200 SD-OCT system (Durham, NC, USA)), with a volume analysis size of $1.4\times1.4$ mm, was centered on the optic nerve head. Systane (Alcon) lubricating drops were used throughout the imaging process.

Analysis of Retinoid Content

All-trans retinal and 11-cis retinal in mouse eyes were extracted using a modification of a previously described method (Bligh and Dyer, 1959). Six-week, post-injection mice were dark-adapted overnight, then under dim-red light, euthanized via CO$_2$ overdose, and eyes enucleated and frozen in liquid N$_2$. Under dim red light and on ice, each eye was homogenized in 1 mL chloroform:methanol:hydroxylamine (2 M) (3:6:1) and incubated at room temperature for 2 minutes. Next, 200 µL chloroform and 240 µL water were added, and each sample was vortexed and centrifuged at 14,000 rpm for 5 minutes. The lower phase was collected, the solvent was evaporated under nitrogen, and the sample was dissolved in hexane. Retinoids in the extracts were identified and quantified by high-performance liquid chromatography (HPLC) analysis, using a Waters Alliance separation module and photodiode array detector with a Supelcosil LC-31 column (25 cm by 4.6 mm by 3 µm) developed with 5% 1,4-dioxane in hexane. Peak identification was done by comparison to retention times of standard compounds and evaluation of wavelength maxima. Quantitative analysis was done by comparison of peak areas at 347 and 351 nm for syn- and anti-11-cis retinal oxime, respectively, and at 357 and 361 nm for syn- and anti-all-trans retinal oxime, respectively (Kurth et al. 2007).

Assay of Retinal Reductase Activity

Mouse retina homogenates were assayed for retinal reductase activity at 6 weeks post-injection. Light-adapted mice were euthanized, and each retina was homogenized individually in 125 µL of 0.25 M sucrose, 25 mM Tris-acetate, pH 7, 1 mM dithiothreitol. The homogenates were centrifuged at 1000×g for 5 minutes to remove unbroken cells, and then the supernates were sonicated with a microtip probe (30 times for 1 second each) on ice. Protein concentrations were determined by a modification of the Lowry procedure (Peterson et al. 1977), and levels of RDH12 were evaluated by western blot. Like samples were pooled and 20 µg of each pooled lysate was assayed (in triplicate) in buffer containing 200 µM all-trans retinal and 200 µM NADPH in HEPES buffer (pH 8); reactions were incubated for 0-45 minutes in a 37° C. water bath (a reaction temperature that minimized thermal isomerization of the retinoid substrates, as well as enzyme inactivation). All-trans retinol formation was quantitated using normal-phase HPLC analysis with comparison to known standards (Chrispell et al. 2009).

Example 1

AAV-Mediated Expression of Human RDH12

A variety of vectors for RDH12-replacement therapy were developed and tested. The optimal RDH12 vector construct is shown in FIG. 2A. It comprises the human RDH12 cDNA under control of a human Rhodopsin Kinase (GRK1) promoter fragment. The construct is packaged in an AAV2/5 serotype. The AAV serotype 5 capsid has been shown to mediate photoreceptor transduction, but with slower kinetics and less robust expression compared to the AAV8 capsid (Yang et al. 2002; Lotery et al. 2003; Allocca et al. 2007; Lebherz et al. 2008). Human RDH12 protein expression in mouse retinas 6 weeks following sub-retinal injection of AAV2/5-hGRK1p.hRDH12 ($1.3\times10^9$ vg) was evaluated using antibodies specific for the mouse Rdh12 or the human RDH12 proteins. Vector-delivered levels of human RDH12 appear to be roughly comparable to the amount of mouse Rdh12 (FIG. 2B). Indirect immunofluorescence imaging on retinal sections was used to evaluate native mouse Rdh12 and recombinant human RDH12, using species-specific antibodies. Localization of endogenous and recombinant RDH12 appears to be identical, indicating that the protein is being processed normally (FIG. 2C).

Figure 3:
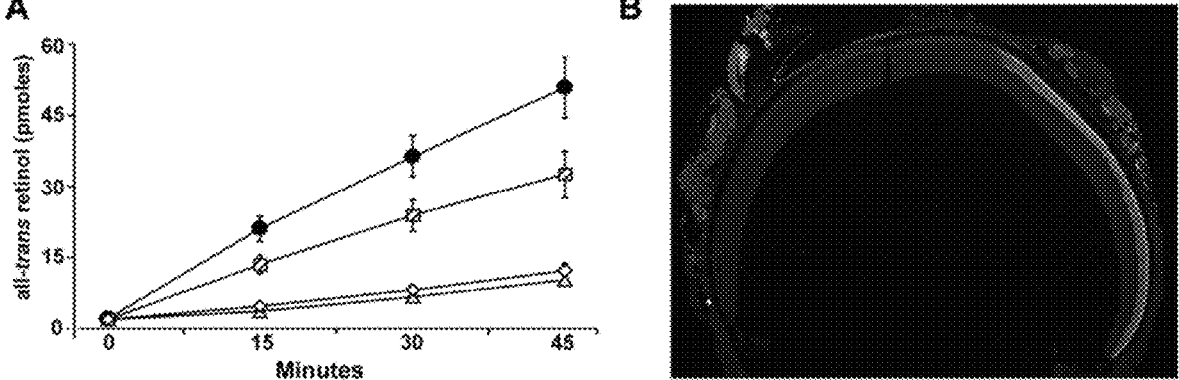
FIG. 3. AAV2/5-hGRK1p.hRDH12 gene-replacement therapy restores RDH12 function in Rdh12-deficient mice. (A) HPLC analysis of retinal reductase activity in retinas from C57BL/6J and Rdh12$^{-/-}$ mice injected with AAV2/5-hGRK1p.hRDH12 ($1.3 \times 10^9$ vg) or PBS, or non-injected. At 6 weeks post-injection, all-trans retinol formation was quantitated in assays with all-trans retinal as a substrate. Each data point represents the mean±standard error for a minimum of 5 independent experiments where retinas from 3 to 5 mice were pooled and assayed in triplicate. ● C57BL/6J; Δ Rdh12$^{-/-}$; ◇ Rdh12$^{-/-}$ PBS-injected; ▨ Rdh12$^{-/-}$ AAV-injected. (B) Immunohistochemistry of recombinant RDH12 expression in an Rdh12$^{-/-}$ mouse whole-retina section evaluated 16 weeks post-injection of AAV2/5-hGRK1p.hRDH12. Human RDH12 (light gray) localizes to the IS, ONL, and OPL of the injected region of the retina (right-hand side of the image).

The capacity of retinas of Rdh12$^{-/-}$ mice to reduce exogenous retinaldehydes is significantly reduced compared to wild-type mice (Chrispell et al. 2009). Six weeks after subretinal injection of $1.3\times10^9$ vg AAV2/5-hGRK1p.hRDH12 into Rdh12$^{-/-}$ mice, retinal homogenates were assayed for in vitro retinal reductase activity. All-trans retinol formation was quantitated using normal-phase HPLC analysis. Each data point represents the mean±standard error for a minimum of 5 independent experiments where retinas from 3 to 5 mice were pooled and assayed in triplicate. Initial rates of all-trans retinol formation in retinas from uninjected Rdh12$^{-/-}$ and C57BL/6J mice were 0.013 pmol minute$^{-1}$ µg protein$^{-1}$, and 0.071 pmol minute$^{-1}$ µg protein$^{-1}$, respectively (FIG. 3A). The residual activity present in Rdh12$^{-/-}$ mice reflects the presence of other RDH isoforms that are capable of reducing all-trans retinal (Rattner et al. 2000; Haeseleer et al. 2002). In Rdh12$^{-/-}$ mice injected with AAV2/5-hGRK1p.hRDH12, the rate of all-trans retinol formation of 0.046 pmol minute$^{-1}$ µg protein$^{-1}$ was significantly greater than for PBS injected Rdh12$^{-/-}$ mice (0.016 pmol minute$^{-1}$ µg protein$^{-1}$). The recovery of retinal reductase activity (about 50%) is consistent with the partial transduction of the retina (about 30%) and indicated that the vector restored normal levels of activity in transduced photoreceptors. The transgene was expressed for over 12 months (longest time point examined). Immunofluorescence labelling showed the extent of retinal transduction and recombinant RDH12 expression in an Rdh12$^{-/-}$ mouse evaluated at 16 weeks post-injection covering approximately one-third of the retinal surface (FIG. 3B).

Figure 4:
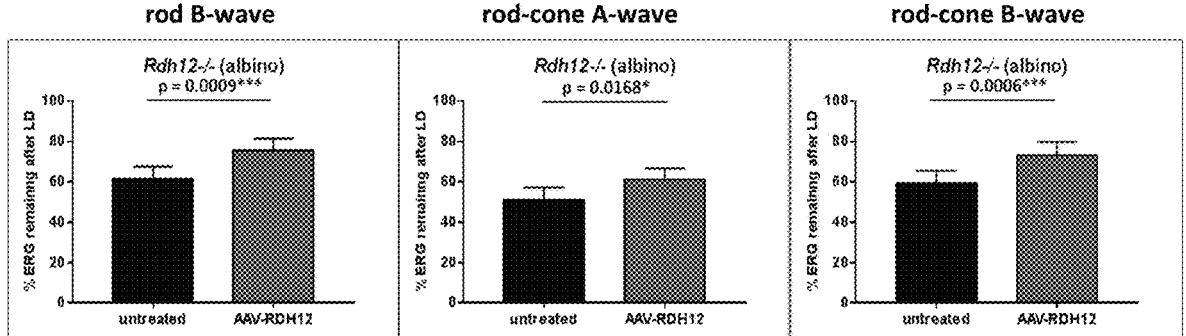
FIG. 4. AAV2/5-hGRK1p.hRDH12 gene-replacement therapy reduces light-damage in albino Rdh12-deficient mice. ERG analysis was performed, one week before and one week after exposure to 5,000 lux for 2 hours, on mice that were injected in one eye with AAV2/5-hGRK1p.hRDH12 and were uninjected in the contralateral eye. Scotopic (rod-isolated and combined rod-cone) responses were quantified for groups of 10-13 mice, and the percentage of the initial ERG response remaining after light damage was calculated. Averaged outcomes with standard errors are shown, as well as the significance of the differences between injected and uninjected eyes calculated using two-tailed paired t-test analysis.

The effect of AAV2/5-hGRK1p.hRDH12 on susceptibility to light-induced damage was evaluated in albino Rdh12$^{-/-}$ mice that were injected in one eye with 1.3×10$^9$ vg or an equal volume of PBS, and received no treatment in the contralateral eye. ERG analysis of scotopic retinal activity (rod-isolated and combined rod-cone) was performed 1 week before, and 1 week after, subjecting the mice to light levels that cause significant retinal damage in albino animals (5,000 lux for 2 hours). The percent retinal activity remaining in vector-treated eyes was significantly greater than that remaining in untreated eyes (p≤0.0168) (FIG. 4). In contrast, in control animals injected with PBS, the percent of scotopic retinal activity remaining in uninjected eyes was not significantly greater than in untreated eyes (p≥0.2255). These findings are consistent with AAV2/5-hGRK1p.hRD12-mediated protection against increased susceptibility to light-induced damage associated with RDH12 deficiency.

Toxicity of the vector was assessed through the direct effect of human RDH12 activity on retinoid metabolism, and for indirect effects on retinal structure and retinal function, as described in the following passage.

Figure 5:
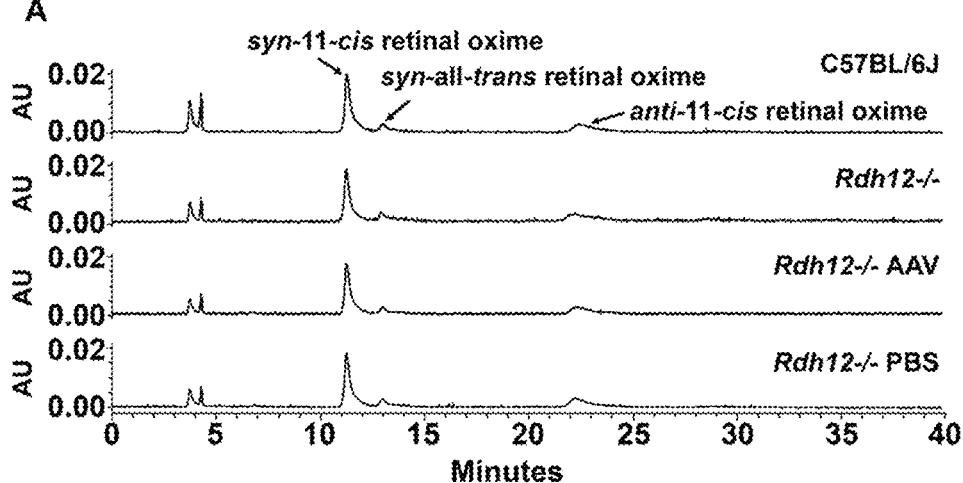
FIG. 5. AAV2/5-hGRK1p.hRDH12 does not significantly affect steady-state levels of 11-cis retinal in the retina. Mice received AAV2/5-hGRK1p.hRDH12 ($1.3 \times 10^9$ vg) or PBS via sub-retinal injection, or were non-injected. Following overnight dark adaptation, retinoids were extracted under dim-red light, and quantified by HPLC analysis. (A) Representative chromatograms from each treatment condition; peaks for syn-11-cis retinal oxime, anti-11-cis retinal oxime, and syn-all-trans retinal oxime are indicated. Total retinal levels of (B) 11-cis retinal and (C) all-trans retinal for each treatment condition±standard error (■ C57BL/6J non-injected; ▨ Rdh12$^{-/-}$ non-injected; ▨ Rdh12$^{-/-}$ AAV injected; □ Rdh12$^{-/-}$ PBS injected).
Figure 5:
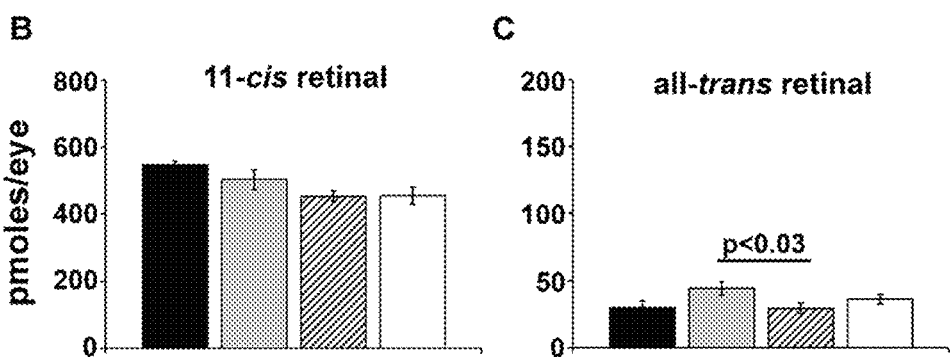
Figure 6:
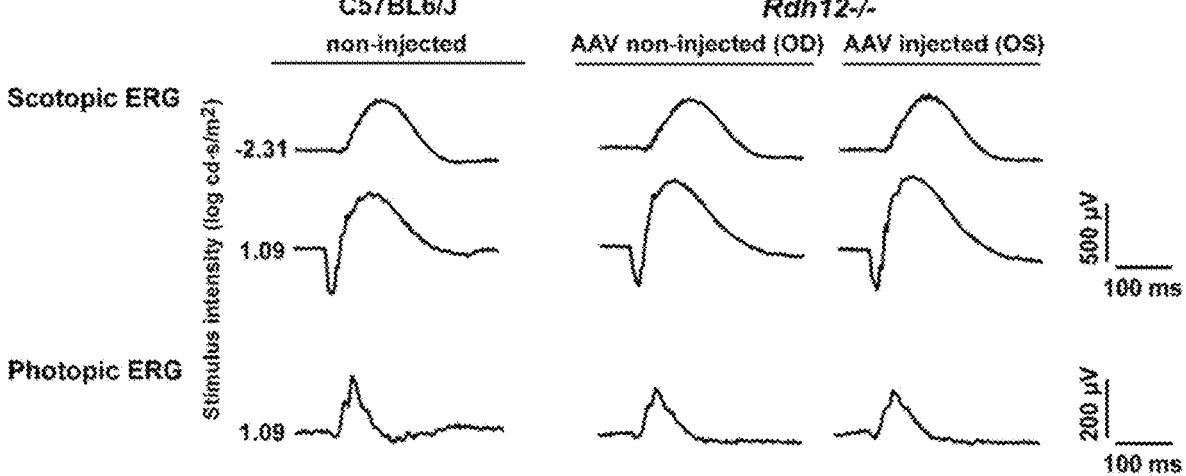
FIG. 6. Retinal function is not adversely affected by AAV2/5-hGRK1p.hRDH12. Scotopic (rod-isolated and combined rod-cone) and photopic (cone-mediated) electroretinogram (ERG) responses recorded at 6 weeks post treatment from C57BL/6J, non-injected; Rdh12$^{-/-}$, non-

The broad substrate specificity of RDH12 that enables the reduction of both 11-cis retinal and all-trans retinal created the potential for overexpression or mislocalization of recombinant protein to negatively impact visual cycle function. HPLC analysis of retinoid content was used to evaluate visual-cycle activity in eyes from Rdh12$^{-/-}$ mice injected with AAV2/5-hGRK1p.hRDH12, or with PBS, or from uninjected C57BL/6J controls. Analysis of retinoids at 6 weeks post-subretinal-injection of AAV2/5-hGRK1p.hRDH12 (1.3×10$^9$ vg) into Rdh12$^{-/-}$ mice showed that hRDH12 expression did not significantly affect the steady state 11-cis retinal levels in the retina (FIG. 5A). A representative chromatogram shows various controls with elution times for various retinoids indicated. Total retinal levels of 11-cis retinal and all-trans retinal represent average values±standard error for a minimum of 5 independent experiments (FIGS. 5B,C). ERG responses of retinal activity were measured in C57BL/6J and Rdh12$^{-/-}$ mice that received 1.3×10$^9$ vg of AAV2/5-hGRK1p.hRDH12 and were maintained in vivarium housing (12-hour dark/12-hour light (<20 lux)). Scotopic (rod-isolated −2.3 log cd·s·m$^{-2}$ stimulus), combined rod-cone (1.09 log cd·s·m$^{-2}$ stimulus), and photopic (cone-mediated responses, 1.09 log cd·s·m$^{-2}$ stimulus) ERGs from a representative animal in each treatment group measured at 6 weeks post-injection showed no significant effect of human RDH12 expression on retinal function (FIG. 6).

Mislocalization of rhodopsin and cone opsin is a well-characterized indicator of decreased photoreceptor cell viability (Adamian et al. 2006; Turney et al. 2007; Brunner et al. 2010; Lopes et al. 2010). Immunohistochemical localization of rhodopsin and red/green opsin was evaluated in Rdh12$^{-/-}$ mice that were non-injected or AAV2/5-hGRK1p.hRDH12-injected (1.3×10$^9$ vg). In mice exhibiting robust transgene expression, no decrease in opsin expression levels or evidence of rod and cone opsin mislocalization were observed at 16 weeks post-treatment; retinal structure remained intact at 54 weeks post-injection (FIG. 7).

Optical coherence tomography (OCT) analysis of C57BL/6J and Rdh12$^{-/-}$ mice evaluated at 54 weeks post-injection of AAV2/5-hGRK1p.hRDH12 (2×10$^9$ vg) showed no gross alterations in retinal lamination across a wide area including both sides of the optic nerve. Retinal structure was stable for at least one year post-injection when compared to uninjected contralateral eyes (FIG. 8).

Example 2. Retinal Damage Caused by AAV2/8

Retinal Damage in AAV2/8-hGRK1p.hRDH12 Injected Mice.

A capsid derived from AAV serotype 8 has been shown to mediate efficient and robust transduction of photoreceptor cells (Allocca et al. 2007; Natkunarajah et al. 2008; Vandenberghe et al. 2011; Vandenberghe et al. 2013). Initial studies were performed with a AAV2/8 serotype carrying the vector construct described above. Rdh12$^{-/-}$ mice treated by subretinal injection of AAV2/8-hGRK1p.hRDH12 at doses of 10$^8$-10$^9$ viral genomes (vg) resulted in robust expression of recombinant human RDH12 protein. However, the injected eyes developed significant retinal damage starting as early as 3 weeks post-injection, and in almost all cases by 6 weeks post-injection. Macrophage infiltration was observed in the majority of cases by the presence of CD68$^+$ cells (FIG. 9). Retinal damage was not mitigated by systemic administration of cyclosporin (Borel et al. 1976) to Rdh12$^{-/-}$ mice continuously from the time of weaning to the time of sacrifice, indicating that immune responses against the vector or the transgene were not the cause of damage. This view is consistent with outcomes obtained in wild-type C57BL/6J mice injected with constructs encoding either human RDH12 (AAV2/8-hGRK1p.hRDH12) or mouse Rdh12 (AAV2/8-hGRK1p.mRdh12), in which significant retinal thinning and macrophage infiltration also occurred by 6 weeks post-injection.

REFERENCES

ADAMIAN M, PAWLYK B S, HONG D H, BERSON E L. (2006). Rod and cone opsin mislocalization in an autopsy eye from a carrier of X-linked retinitis pigmentosa with a Gly436Asp mutation in the RPGR gene. Am J Ophthalmol 142, 515-8.

ACLAND G M, AGUIRRE G D, RAY J, ZHANG Q, et al. (2001). Gene therapy restores vision in a canine model of childhood blindness. Nat Genet 28, 92-5.

ALEXANDER J J, UMINO Y, EVERHART D, CHANG B, et al. (2007). Restoration of cone vision in a mouse model of achromatopsia. Nat Med 13, 685-7.

ALI R R, SARRA G M, STEPHENS C, ALWIS M D, et al. (2000). Restoration of photoreceptor ultrastructure and function in retinal degeneration slow mice by gene therapy. Nat Genet 25, 306-10.

ALLOCCA M, MUSSOLINO C, GARCIA-HOYOS M, SANGES D, et al. (2007). Novel adeno-associated virus serotypes efficiently transduce murine photoreceptors. J Virol 81, 11372-80.

BAINB RIDGE J W, SMITH A J, BARKER S S, ROBBIE S, et al. (2008). Effect of gene therapy on visual function in Leber's congenital amaurosis. N Engl J Med 358, 2231-9.

BELTRAN W A, CIDECIYAN A V, LEWIN A S, IWABE S, et al. (2012). Gene therapy rescues photoreceptor blindness in dogs and paves the way for treating human X-linked retinitis pigmentosa. Proc Natl Acad Sci USA 109, 2132-7.

BEN-SHABAT S, PARISH C A, HASHIMOTO M, LIU J, et al. (2001). Fluorescent pigments of the retinal pigment epithelium and age-related macular degeneration. Bioorg Med Chem Lett 11, 1533-40.

BELYAEVA O V, KORKINA O V, STETSENKO A V, KIM T, et al. (2005). Biochemical properties of purified human retinol dehydrogenase 12 (RDH12): catalytic efficiency toward retinoids and C9 aldehydes and effects of cellular retinol-binding protein type I (CRBPI) and cellular retinaldehyde-binding protein (CRALBP) on the oxidation and reduction of retinoids. Biochemistry 44, 7035-47.

BLIGH E G, DYER W J. (1959). A rapid method of total lipid extraction and purification. Can J Biochem Physiol 37, 911-7.

BOREL J F, FEURER C, GUBLER H U, STÄHELIN H. (1976). Biological effects of cyclosporin A: a new anti-lymphocytic agent. Agents Actions 6, 468-75.

BRUNNER S, SKOSYRSKI S, KIRSCHNER-SCHWABE R, KNOBELOCH K P, et al. (2010). Cone versus rod disease in a mutant Rpgr mouse caused by different genetic backgrounds. Invest Ophthalmol Vis Sci, 51, 1106-15.

CARLSON N B, KURTZ D, HEATH D A, HINES C. in: Clinical Procedures for Ocular Examination. 3rd Ed. Appleton & Lange, Norwalk, CT; 1990:63-77.

CHEN C, THOMPSON D A, KOUTALOS Y. (2012). Reduction of all-trans-retinal in vertebrate rod photoreceptors requires the combined action of RDH8 and RDH12. J Biol Chem, 287, 24662-70.

CHEN Y, OKANO K, MAEDA T, CHAUHAN V, et al. (2012). Mechanism of all-trans-retinal toxicity with implications for stargardt disease and age-related macular degeneration. J Biol Chem 287, 5059-69.

CHRISPELL J D, FEATHERS K L, KANE M A, KIM, C Y, et al. (2009). Rdh12 activity and effects on retinoid processing in the murine retina. J Biol Chem 284, 21468-77.

CIDECIYAN A V, ALEMAN T S, BOYE S L, SCHWARTZ S B, et al. (2008). Human gene therapy for RPE65 isomerase deficiency activates the retinoid cycle of vision but with slow rod kinetics. Proc Natl Acad Sci USA 105, 151 12-7.

DEN HOLLANDER A I, ROEPMAN R, KOENEKOOP R K, CREMERS F P. (2008). Leber congenital amaurosis: genes, proteins and disease mechanisms. Prog Retin Eye Res 27, 391-419.

FLOTTE T R, SOLOW R, OWENS R A, AFIONE S, et al. (1992). Gene expression from adeno-associated virus vectors in airway epithelial cells. Am J Respir Cell Mol Biol 7, 349-56.

FLOTTE T R, AFIONE S A, SOLOW R, DRUMM M L, et al. (1993). Expression of the cystic fibrosis transmembrane conductance regulator from a novel adeno-associated virus promoter. J Biol Chem 268, 3781-90.

HAESELEER F, JANG G F, IMANISHI Y, DRIESSEN C A, et al. (2002). Dual-substrate specificity short chain retinol dehydrogenases from the vertebrate retina. J Biol Chem 277, 45537-46.

HERMONAT P L, MUZYCZKA N. (1984). Use of adeno-associated virus as a mammalian DNA cloning vector: transduction of neomycin resistance into mammalian tissue culture cells. Proc Natl Acad Sci USA 81, 6466-70.

JANECKE A R, THOMPSON D A, UTERMANN G, BECKER C, et al. (2004). Mutations in RDH12 encoding a photoreceptor cell retinol dehydrogenase cause childhood-onset severe retinal dystrophy. Nat Genet 36, 850-854.

JOHNSON D D. Deafness and Vision Disorders: Anatomy and Physiology, Assessment Procedures, Ocular Anomalies, and Educational Implications, Charles C. Thomas Publisher;

KELLER B, ADAMSKI J. (2007). RDH12, a retinol dehydrogenase causing Leber's congenital amaurosis, is also involved in steroid metabolism. J Steroid Biochem Mol Biol 104, 190-4.

KHANI S C, PAWLYK B S, BULGAKOV O V, KASPEREK E, et al. (2007). AAV-mediated expression targeting of rod and cone photoreceptors with a human rhodopsin kinase promoter. Invest Ophthalmol Vis Sci 48, 3954-61.

KOENEKOOP R K. (2004). An overview of Leber congenital amaurosis: a model to understand human retinal development. Sury Ophthalmol 49, 379-98.

KOMAROMY A M, ALEXANDER J J, ROWLAN J S, GARCIA M M, et al. (2010). Gene therapy rescues cone function in congenital achromatopsia. Hum Mol Genet 19, 2581-93.

KUMARAN N, MOORE A T, WELEBER R G, MICHAELIDES M. (2017). Leber congenital amaurosis/early-onset severe retinal dystrophy: clinical features, molecular genetics and therapeutic interventions. Br J Ophthalmol 101, 1147-1154.

KURTH I, THOMPSON D A, RUTHER K, FEATHERS K L, et al. (2007). Targeted disruption of the murine retinal dehydrogenase gene Rdh12 does not limit visual cycle function. Mol Cell Biol 27, 1370-9.

LEBHERZ C, MAGUIRE A, TANG W, BENNETT J, et al. (2008). Novel AAV serotypes for improved ocular gene transfer. J Gene Med 10, 375-82.

LEE S A, BELYAEVA O V, KEDISHVILI N Y. (2008). Effect of lipid peroxidation products on the activity of human retinol dehydrogenase 12 (RDH12) and retinoid metabolism. Biochim Biophys Acta 1782, 421-5.

LHERITEAU E, LIBEAU L, STIEGER K, DESCHAMPS J Y, et al. (2009). The RPGRIP 1-deficient dog, a promising canine model for gene therapy. Mol Vis 15, 349-61.

LOPES V S, JIMENO D, KHANOBDEE K, SONG X, et al. (2010). Dysfunction of heterotrimeric kinesin-2 in rod photoreceptor cells and the role of opsin mislocalization in rapid cell death. Mol Biol Cell 21, 4076-88.

LOTERY A J, YANG G S, MULLINS R F, RUSSELL S R, et al. (2003). Adeno-associated virus type 5: transduction efficiency and cell-type specificity in the primate retina. Hum Gene Ther 14, 1663-71.

MACKAY D S, DEV BORMAN A, MORADI P, HENDERSON R H, et al. (2011). RDH12 retinopathy: novel mutations and phenotypic description. Mol Vis 17, 2706-16.

MAEDA A, MAEDA T, IMANISHI Y, SUN W, et al. Retinol dehydrogenase (RDH12) protects photoreceptors from light-induced degeneration in mice. J Biol Chem 281, 37697-704.

MAGUIRE A M, SIMONELLI F, PIERCE E A, PUGH E N, J R., et al. (2008). Safety and efficacy of gene transfer for Leber's congenital amaurosis. N Engl J Med 358, 2240-8.

MARCHETTE L D, THOMPSON D A, KRAVTSOVA M, NGANSOP T N, et al. (2010). Retinol dehydrogenase 12 detoxifies 4-hydroxynonenal in photoreceptor cells. Free Radic Biol Med 48, 16-25.

MCLAUGHLIN S K, COLLIS P, HERMONAT P L, MUZYCZKA N. (1988). Adeno-associated virus general transduction vectors: analysis of proviral structures. J Virol 62, 1963-73.

MACKENZIE D, ARENDT A, HARGRAVE P, MCDOW-ELL J H, et al. (1984). Localization of binding sites for carboxyl terminal specific anti-rhodopsin monoclonal antibodies using synthetic peptides. Biochemistry 23, 6544-9.

MACLAREN R E, GROPPE M, BARNARD A R, COT-TRIALL C L, et al. (2014). Retinal gene therapy in patients with choroideremia: initial findings from a phase 1/2 clinical trial. Lancet 383, 1129-37.

MUZYCZKA N. (1992). Use of adeno-associated virus as a general transduction vector for mammalian cells. Curr Top Microbiol Immunol 158, 97-129.

NATKUNARAJAH M, TRITTIBACH P, MCINTOSH J, DURAN Y, et al. (2008). Assessment of ocular transduction using single-stranded and self-complementary recombinant adeno-associated virus serotype 2/8. Gene Ther 15, 463-7.

NISHIGUCHI K M, CARVALHO L S, RIZZI M, POWELL K, et al. (2015). Gene therapy restores vision in rd1 mice after removal of a confounding mutation in Gpr179. Nat Commun 6, 6006. PANG J J, LEI L, DAI X, SHI W, et al. (2012). AAV-mediated gene therapy in mouse models of recessive retinal degeneration. Curr Mol Med 12, 316-30.

PAWLYK B S, SMITH A J, BUCH P K, ADAMIAN M, et al. (2005). Gene replacement therapy rescues photoreceptor degeneration in a murine model of Leber congenital amaurosis lacking RPGRIP. Invest Ophthalmol Vis Sci 46, 3039-45.

PAWLYK B S, BULGAKOV O V, LIU X, XU X, et al. (2010). Replacement gene therapy with a human RPGRIPl sequence slows photoreceptor degeneration in a murine model of Leber congenital amaurosis. Hum Gene Ther 21, 993-1004.

PERRAULT I, HANEIN S, GERBER S, BARBET F, et al. (2004). Retinal dehydrogenase 12 (RDH12) mutations in leber congenital amaurosis. Am J Hum Genet 75, 639-46.

PETERSON G L. (1977). A simplification of the protein assay method of Lowry et al. which is more generally applicable. Anal Biochem 83, 346-56.

RATTNER A, SMALLWOOD P M, NATHANS J. (2000). Identification and characterization of all-trans-retinol dehydrogenase from photoreceptor outer segments, the visual cycle enzyme that reduces all-trans-retinal to all-trans-retinol. J Biol Chem 275, 11034-43.

SAMULSKI R J, CHANG L S, SHENK T. (1989). Helper-free stocks of recombinant adeno-associated viruses: normal integration does not require viral gene expression. J Virol 63, 3822-8.

SCHUSTER A, JANECKE A R, WILKE R, SCHMID E, et al. (2007). The phenotype of early-onset retinal degeneration in persons with RDH12 mutations. Invest Ophthalmol Vis Sci 48, 1824-31.

SPARROW J R. (2010). Bisretinoids of RPE lipofuscin: trigger for complement activation in age-related macular degeneration. Adv Exp Med Biol 703, 63-74.

SUN X, PAWLYK B, XU X, LIU X, et al. (2010). Gene therapy with a promoter targeting both rods and cones rescues retinal degeneration caused by AIPL1 mutations. Gene Ther 17, 117-31.

TAN M H, SMITH A J, PAWLYK B, XU X, et al. (2009). Gene therapy for retinitis pigmentosa and Leber congenital amaurosis caused by defects in AIPL1: effective rescue of mouse models of partial and complete Aipll deficiency using AAV2/2 and AAV2/8 vectors. Hum Mol Genet.

THOMPSON D A, GAL A. (2003). Vitamin A metabolism in the retinal pigment epithelium: genes, mutations, and diseases. Prog Retin Eye Res 22, 683-703.

THOMPSON D A, JANECKE A R, LANGE J, FEATHERS K L, et al. (2005). Retinal degeneration associated with RDH12 mutations results from decreased 11-cis retinal synthesis due to disruption of the visual cycle. Hum Mol Genet 14, 3865-75.

THOMPSON D A, KHAN N W, OTHMAN M I, CHANG B, et al. (2012). Rd9 is a naturally occurring mouse model of a common form of retinitis pigmentosa caused by mutations in RPGR-ORF15. PLoS One 7, e35865.

TRATSCHIN J D, WEST M H, SANDBANK T, CARTER B J. (1984a). A human parvovirus, adeno-associated virus, as a eucaryotic vector: transient expression and encapsidation of the procaryotic gene for chloramphenicol acetyltransferase. Mol Cell Biol 4, 2072-81.

TRATSCHIN J D, MILLER I L, CARTER B J. (1984b). Genetic analysis of adeno-associated virus: properties of deletion mutants constructed in vitro and evidence for an adeno-associated virus replication function. J Virol 51, 611-9.

TRATSCHIN J D, MILLER I L, SMITH M G, CARTER B J. (1985). Adeno-associated virus vector for high-frequency integration, expression, and rescue of genes in mammalian cells. Mol Cell Biol 5, 3251-60.

TURNEY C, CHONG N H, ALEXANDER R A, HOGG C R, et al. (2007). Pathological and electrophysiological features of a canine cone-rod dystrophy in the miniature longhaired dachshund. Invest Ophthalmol Vis Sci 48, 4240-9.

VANDENBERGHE L H, BELL P, MAGUIRE A M, CEAR-LEY C N, et al. (2011). Dosage thresholds for AAV2 and AAV8 photoreceptor gene therapy in monkey. Sci Transl Med 3, 88ra54.

VANDENBERGHE L H, BELL P, MAGUIRE A M, XIAO R, et al. (2013). AAV9 targets cone photoreceptors in the nonhuman primate retina. PLoS One 8, e53463.

XIAO X, LI J, SAMULSKI R J. (1998). Production of high-titer recombinant adeno-associated virus vectors in the absence of helper adenovirus. J Virol 72, 2224-32.

YANG G S, SCHMIDT M, YAN Z, LINDBLOOM J D, et al. (2002). Virus-mediated transduction of murine retina with adeno-associated virus: effects of viral capsid and genome size. J Virol 76, 7651-60.

YOUNG J E, VOGT T, GROSS K W, KHANI S C. (2003). A short, highly active photoreceptor-specific enhancer/promoter region upstream of the human rhodopsin kinase gene. Invest Ophthalmol Vis Sci 44, 4076-85.

WELEBER R G, FRANCIS P J, TRZUPEK K M, BEATTIE C. (2004). Leber Congenital Amaurosis. In: PAGON R A, ADAM M P, ARDINGER H H, WALLACE S E, et al. GeneReviews® [Internet]. Seattle (Wash.): University of Washington, Seattle; 1993-2017. [updated 2013 May 2].

WONDISFORD F E, USALA S J, DECHERNEY G S, CASTREN M, et al. (1988). Cloning of the human thyrotropin beta-subunit gene and transient expression of biologically active human thyrotropin after gene transfection. Mol Endocrinol 2, 32-9.

Each of the references cited herein is hereby incorporated by reference in its entirety or in relevant part, as would be apparent from the context of the citation.

It is to be understood that while the claimed subject matter has been described in conjunction with the detailed description thereof, the foregoing description is intended to illustrate and not limit the scope of that claimed subject matter, which is defined by the scope of the appended claims. Other aspects, advantages, and modifications are within the scope of the following claims.

What is claimed is:

1. A method of reducing or preventing accumulation of all-trans retinal in a human subject having Leber Congenital Amaurosis (LCA) due to one or more loss-of-function mutations in the gene encoding the human Retinol Dehydrogenase 12 (RDH12) protein, the method comprising administering into the subretinal space of at least one eye of the human subject an adeno-associated viral (AAV) vector comprising a nucleic acid, wherein:

the nucleic acid encodes human RDH12 comprising the amino acid sequence set forth in SEQ ID NO:2;
the AAV vector is AAV2/5; and
the nucleic acid is under the expression control of a human rhodopsin kinase 1 (hGRK1) promoter;
thereby reducing or preventing accumulation of all-trans retinal in the human subject.

2. The method of claim 1, wherein the hGRK1 promoter comprises the nucleic acid sequence set forth in SEQ ID NO: 3.

3. The method of claim 2, the method comprising administering the vector at a titer of about $2 \times 10^{10}$ viral genomes per milliliter (vg/mL) to a titer of about $2 \times 10^{12}$ vg/mL.

4. The method of claim 2, wherein the nucleic acid further comprises a polyadenylation signal.

5. The method of claim 4, wherein the polyadenylation signal is a simian virus 40 polyadenylation signal.

6. The method of claim 1, the method comprising administering the vector at a titer of about $2 \times 10^{10}$ viral genomes per milliliter (vg/mL) to a titer of about $2 \times 10^{12}$ vg/mL.

7. The method of claim 6, wherein the nucleic acid further comprises a polyadenylation signal.

8. The method of claim 7, wherein the polyadenylation signal is a simian virus 40 polyadenylation signal.

9. The method of claim 1, wherein a microinjection cannula is inserted into the subretinal space.

10. The method of claim 1, wherein the nucleic acid comprises SEQ ID NO: 1.

11. The method of claim 1, wherein the nucleic acid further comprises a polyadenylation signal.

12. The method of claim 11, wherein the polyadenylation signal is a simian virus 40 polyadenylation signal.

\* \* \* \* \*